US009540640B2

(12) United States Patent
Kandel et al.

(10) Patent No.: US 9,540,640 B2
(45) Date of Patent: Jan. 10, 2017

(54) COMPOSITIONS AND METHODS FOR INHIBITING HYPDXIA INDUCED DAMAGE

(71) Applicants: Health Research, Inc., Buffalo, NY (US); F. Hoffmann-La Roche AG, Basel (CH)

(72) Inventors: Eugene Kandel, Williamsville, NY (US); Evan Zynda, Williamsville, NY (US); Brigitte Schott, Landser (FR)

(73) Assignees: Health Research, Inc., Buffalo, NY (US); F. Hoffmann-La Roche AG, Basel (CH)

(*) Notice: Subject to any disclaimer, the term of this patent is extended or adjusted under 35 U.S.C. 154(b) by 0 days.

(21) Appl. No.: 14/423,739

(22) PCT Filed: Sep. 5, 2013

(86) PCT No.: PCT/US2013/058220
§ 371 (c)(1),
(2) Date: Feb. 25, 2015

(87) PCT Pub. No.: WO2014/039648
PCT Pub. Date: Mar. 13, 2014

(65) Prior Publication Data
US 2015/0299697 A1 Oct. 22, 2015

Related U.S. Application Data

(60) Provisional application No. 61/697,366, filed on Sep. 6, 2012, provisional application No. 61/779,256, filed on Mar. 13, 2013.

(51) Int. Cl.
C12N 15/113 (2010.01)
A61K 31/7088 (2006.01)
A61K 31/713 (2006.01)
A61K 45/06 (2006.01)

(52) U.S. Cl.
CPC ......... *C12N 15/113* (2013.01); *A61K 31/7088* (2013.01); *A61K 31/713* (2013.01); *A61K 45/06* (2013.01); *C12N 2310/14* (2013.01); *C12N 2310/531* (2013.01); *C12N 2320/31* (2013.01)

(58) Field of Classification Search
CPC .. C12N 15/113; A61K 31/7088; A61K 31/713
See application file for complete search history.

(56) References Cited

U.S. PATENT DOCUMENTS

2001/0029013 A1  10/2001 Reed et al.
2005/0287565 A1* 12/2005 Merchiers ............... C12Q 1/25
                                                    435/6.16
2010/0305183 A1* 12/2010 Nimmo ................. A61K 31/00
                                                    514/419

FOREIGN PATENT DOCUMENTS

WO   0016809      3/2000
WO   03/074654 A2 9/2003
WO   2005100986  10/2005
WO   2007080457   7/2007

OTHER PUBLICATIONS

Skuli et al. (Cancer Res. (2006); 66(1):482-489).*
Brummelkamp (Science (2002) 296:550-553).*
Eltzschig, H. K. et al., Hypoxia and Inflammation, The New England Journal of Medicine, Feb. 17, 2011, vol. 364, No. 7, pp. 656-665.
Nakamura, et al., Ubiquitin-like protein MNSFb regulates TLR-2-mediated signal transduction, Molecular and cellular Biochemistry, vol. 364, No. 1-2, pp. 39-43 Jan. 25, 2012.
Nakamura, et al., Characterization of ubiquitin-like polypeptide acceptor protein, a novel pro-apoptotic member of the Bcl2 family, European Jorunal of Biochemistry, vol. 270, No. 20, pp. 4052-4058 Oct. 15, 2003.
Pickard, et al., Dysregulated expression of Fau and MELK is associated with poor prognosis in breast cancer, Breast Cancer Research, vol. 11, No. 4, pp. R60 Aug. 11, 2009.
Gao, et al., Carnitine palmitoyltransferase 1A prevents fatty acid-induced adipocyte dysfunction through suppression of c-Jun N-terminal kinase, Biochemical Journal, vol. 214, No. 3, pp. 723-732 May 1, 2011.
Zheng, et al., Far upstream element binding protein 1 activates translation of p27mRNA through its internal ribosomal entry site, International Journal of Biochemistry and Cell Biology, vol. 43, No. 11, pp. 1641-1648 Aug. 1, 2011.
Lee, et al., Core2 O-Glycan structure is essential for the cell surface expression of Sucrase Isomaltase and Dipeptidyl Peptidase-IV during intestinal cell differentiation, Journal of Biological Chemistry, vol. 285, No. 48, pp. 37683-37692 Nov. 26, 2010.
Skuli, et al., Activation of RhoB by hypoxia controls Hypoxia-Inducible Factor 1a stabilization through Glycogen Synthase Kinase-3 U87 glioblastoma cells, Cancer Research, vol. 66, No. 1, pp. 482-489 Jan. 1, 2006.
Lejen, et al., An antisense oligodeoxynucleotide targeted to chromaffin cell scinderin gene decreased scinderin levels and inhibited depolarization-induced cortical F-actin disassembly and exocytosis, Journal of Neurochemistry, vol. 76, Vo. 3, pp. 768-777 Feb. 1, 2001.

(Continued)

Primary Examiner — Jon E Angell
(74) Attorney, Agent, or Firm — Hodgson Russ LLP

(57) ABSTRACT

Provided are compositions and methods for inhibiting hypoxia-induced damage. The compositions and methods involve the use of one or more agents that can inhibit one or any combination of the genes BCL2L14, BLOC1S2, C20RF42, CPT1A, FBP1, GCNT3, RHOB, SCIN, TACR1 and TNFAIP6. Polynucleotide and non-polynucleotide agents which can be used for inhibiting one or more of the genes are included. The method involves introducing one or more gene inhibiting agents to a cell, tissue, organ, or individual such that formation of hypoxia related damage is inhibited. Kits which contain the agents and printed information about using them for inhibiting hypoxia induced damage are also included.

6 Claims, 11 Drawing Sheets

(56) References Cited

OTHER PUBLICATIONS

Naono-Nakayama, et al., Knockdown of the tachykinin neurokinin 1 receptor by intrathecal administration of small interfering RNA in rats, European Journal of Pharmacology, vol. 670, No. 2, pp. 448-457 Sep. 13, 2011.
Robinson, et al., Potentiation of brain stimulation reward by morphine effects of neurokinin-1 receptor antagonism, Psychopharmacology, vol. 220, No. 1, pp. 215-224 Sep. 10, 2011.
Guo, et al., TSG-6 controls transcription and activation of Matrix Metalloproteinase 1 in conjunctivochalasis, IOVS, vol. 53, No. 3, pp. 1372-1380 Mar. 1, 2012.
Zynda, et al., An RNA interference screen identities new avenues for nephroprotection, Cell Death and Differentiation, vol. 23, No. 4, pp. 608-615 Nov. 13, 2015.

\* cited by examiner

SEQUENCE LISTING

```
<160> NUMBER OF SEQ ID NOS: 27

<210> SEQ ID NO 1
<211> LENGTH: 1886
<212> TYPE: DNA
<213> ORGANISM: Homo sapiens

<400> SEQUENCE: 1
aatgacatga cagccattcc gtggccaggg acaccactgc ccaagctgga gaccacgagg      60
attcagggac tgaagccagc atgggaattc ctggtttgag atcagagtcc tgagtacctc     120
gtgggaactt gggcactcat ccgcaggagg tctagacccc cagagaattc cttgagtcta     180
aggcacaggc ccaacatgtg tagcaccagt gggtgtgacc tggaagaaat ccccctagat     240
gatgatgacc taaacaccat agaattcaaa atcctcgcct actacaccag acatcatgtc     300
ttcaagagca cccctgctct cttctcacca aagctgctga gaacaagaag tttgtcccag     360
aggggcctgg ggaattgttc agcaaatgag tcatggacag aggtgtcatg gccttgcaga     420
aattcccaat ccagtgagaa ggccataaac cttggcaaga aaaagtcttc ttggaaagca     480
ttctttggag tagtggagaa ggaagattcg cagagcacgc ctgccaaggt ctctgctcag     540
ggtcaaagga cgttggaata ccaagattcg cacagccagc agtggtccag gtgtctttct     600
aacgtggagc agtgcttgga gcatgaagct gtggacccca aagtcatttc cattgccaac     660
cgagtagctg aaattgttta ctcctggcca ccaccacaag cgacccaggc aggaggcttc     720
aagtccaaag agattttgt aactgagggt ctctccttcc agctccaagg ccacgtgcct     780
gtagcttcaa gttctaagaa agatgaagaa gaacaaatac tagccaaaat tgttgagctg     840
ctgaaatatt caggagatca gttggaaaga aagctgaaga aagataaggc tttgatgggc     900
cacttccagg atgggctgtc ctactctgtt ttcaagacca tcacagacca ggtcctaatg     960
ggtgtggacc ccaggggaga atcagaggtc aaagctcagg gctttaaggc tgcccttgta    1020
atagacgtca cggccaagct cacagctatt gacaaccacc cgatgaacag ggtcctgggc    1080
tttggcacca agtacctgaa agagaacttc tcgccatgga tccagcagca cggtggatgg    1140
gaaaaaatac ttgggatatc acatgaagaa gtagactgaa atatcagatt tgtcatcagg    1200
aatactcttt gtctactgtg gtcctgtgca cgttggcctc agatggacta caggagatta    1260
caacgtacaa ggcagatgga gcattgacgt tttcaaaacc attattcctg tgactggaga    1320
ggcatcagga gaggtctcgt tcgtctccag ctcataaaat gtagcagcat catccttgac    1380
agtgatgttt tcaggcccct ccattgagaa cctgaggaaa tctgtaaaga taagtggtga    1440
tgttgtttca aacgttcaga acagatacca tcatcctgcc tttgttagct gctgtaggga    1500
```

```
aagtgcgtta cagatgtctg ctgacctcac aagagtgaaa agataaactg tgcatgtgtt   1560
tccacttccg tttctagtac tatttatttt taaactacac ttggggtggc ctaataccta   1620
ggaagatgtt gctattcacg ttagtaaaca gcctaaagaa actcttaggt ttactgctac   1680
atccatttgt ttggagaggt aactgttgtc tgtgcctttt tgaaaaactt ccatttggta   1740
caaaattttt actccaacac cccctcaacc ctttctcag ggaccacacc tcttcttccc    1800
aaggtccctg ggacttcctc attctttgtg gtagtacaat gattggtagc aggtaaaata   1860
aatacataga aagactactg tcaaaa                                        1886

<210> SEQ ID NO 2
<211> LENGTH: 2679
<212> TYPE: DNA
<213> ORGANISM: Homo sapiens

<400> SEQUENCE: 2
acacccagtg cgcatgcgca gcaccccggc ccggaaacag cgcggggtcc gctatggcgg     60
cggcagccga gggcgtactg gcgacccgga gtgatgagcc cgcccgagac gatgccgccg    120
tggagacagc tgaggaagca aaggagcctg ctgaagctga catcactgag ctctgccggg    180
acatgttctc caaaatggcc acttacctga ctggggaact gacggccacc agtgaagact    240
ataagctcct ggaaaatatg aataaactca ccagcttgaa gtatcttgaa atgaaagata    300
ttgctataaa cattagtagg aacttaaagg acttaaacca gaaatatgct ggactgcagc    360
cttatctgga tcagatcaat gtcattgaag agcaggtagc agctcttgag caggcagctt    420
acaagttgga tgcatattca aaaaaactgg aagccaagta caagaagctg gagaagcgat    480
gagaaactta tttctatggg acagagtctt tttttttaa tgtggaagaa tgtcttataa    540
aacctgaatc ctgaggctga tgaattgtga aaattcctca aaaggaaatt atgctggtca    600
tcacaggaac atctcaacgt tcgagtaaac tggaggactg tggctattcc tgaaccttct    660
ttgagacaga atccctcaga atctcacact tataacttcc tacctttac ttgaatgctt    720 tgccatattc aggacagaga ctctcacaaa gttcagaaaa cagctggact taccagtaaa    780
atcaaatgag aggaccctatt ttctctggta gtggttgatt actacattat tttcttaagt    840
ggctggtttt ttagttacta tgtaaatggt cgttttctg ttaatgatgc taatgtgttg    900
taaacaagat tctaaattta aaaggaaaa caaaacaaac ttgttctttg cagcttatca    960
ccttgtgaat gtcggtaact tacttttcca taatattgca ataacataa atcttaaaa    1020 taattccaag ctgagtcttc tagattgagc agaaatggtg aaaggagtat tgataacttg   1080
gcgtatgtga tgggccctc ttgtttattt tctatgtgag tcacattgac atgcgatcag    1140
tttgggaaat gtgatgaaaa caaagactag atgggtatgt gtgtttatgt gttgggtagg   1200
gaggtgacga ttgccactca taaaataaag gatttataa aataccttcc tactgtgtat   1260
gtaggatttg gggggatctt agggacctaa tcgacttctt tgcacactaa aaacatcaga   1320
caatgggaca tactgactga ccagtctagg ttgaaagata ggcagcctta cccagaacac   1380
aacattagca gctgggaagg tgtctgaggt ccccaattac atatcccaaa gagtttctta   1440
cttctgtttc tgtcatttcc cctctgttcc agacagtcat catttatcct ctgttcttcc   1500
tggactgttg ctgtggtctc ttctcatctt aactgtccct tccaaccacc ctccacactg   1560
ctgccagagc aatcttaaaa atgtaaactg gccctattac tcctgcttag aaccctgtag   1620
tgacttatca tggcctctga aaaatctaga cttttcattat gcatacaagt cccttgtgtt   1680
tttttgtttg tttatagaca gggtctctat tgtcacccag gctggagtgt ggtggtgtga   1740
```

```
taatagctca ccttgacctc ctaggctcaa ctgatcttcc cacctcagcc tcctgaatag    1800
ctgggactac cagcacgctc caccatgcct tgctaattat tttttataca gatggagtct    1860
cactatgttg tccaggctgg tcttgaactg gcctcaagtg attctcttac cacagcctgc    1920
cagagtgctg agattgtagg catgaaccac cgtgcctaac ataaggcccc tatttaaaca    1980 ttttcttaa ataaaaaaca aagaattaa actgtaactc tactatctta acatagaatc      2040
```
(ttttcttaa ataaaaaaca aagaattaa actgtaactc tactatctta acatagaatc   2040)
```
agtcttaccc cttcttccaa ccctttcct tttccgtgca tgtattgatc tatttttttt     2100
ttttttttga gatgaagtct tgctctgtcg cctgggctgg agtgcagtgg tgcgatctta    2160
gctcactgca acctctgttt cctgggttca agcgattctc ctgcctcagc ctcccgagta    2220
gttgagattt acaggtgccc accaccatgc caggctaatt tttgtatttt tagtagagac    2280
ggggtttcac catgttggcc aggctggtct cgaactcctg accccaaatg atccacccac    2340
ctcggcctcc caaagtgctg ggattacagg tgtgagccac cgcacccagc catgttgatc    2400 tattttaaa aagttttat ttcctgttac actgtgttca gctatcttca gccaccttaa      2460
attcccatgg atgagttttc ataaactttt tgaaaataga tttagattta cgggaaagtt    2520
gcaaagataa tacagaattt aatggatgag ttttttatt gatgtgtaat agatgtatgt     2580
attttcagag tacaagtgat aatttaatac atgtatataa tgtgtaaata ttaaatcaag    2640
agttattggg atgtccttca ccttaaaaaa aaaaaaaa                            2679
```

<210> SEQ ID NO 3
<211> LENGTH: 2540
<212> TYPE: DNA
<213> ORGANISM: Homo sapiens

<400> SEQUENCE: 3

```
agtttggccc cgtttgtaaa aggccgcggc aggcgaagag agaagagact atcaagatct     60
ccacttaggg aagtgggaat cttatttgcg gaacattggg cagaagcttt gccattggct    120
ggtggagaag gaggaggcag aatgtctgca ttgttacacc atacagctca aacttcagaa    180
gattttgggt taagcagtta tcattagtct gcaaatgatc gtgttttcac ctgatcatta    240
gaaactaatg aaacaccttt taagtcttat gaattcaggt tacactgttt tccagatgcc    300
ttggcagctg gtacagggcc tctgaaaaat ggaaccaaat tctctgagga ctaaagtccc    360
agcttcctta tctgatttgg ggaaggccac attgagggga atcagaaagt gtccccgatg    420
tggcacatac aatggaaccc ggggactgag ctgtaagaac aagacatgtg aaccatatt    480
```
(tggcacatac aatggaaccc ggggactgag ctgtaagaac aagacatgtg aaccatatt 480)
```
ccgctacggt gcacgcaagc agcctagtgt tgaagctgtc aaaatcatta caggctctga    540
tcttcaggtc tactcagtgc ggcaaagaga ccggggcccct gattaccgat gctttgtgga   600
gctcggggtt tcagagacaa caatccagac agtggatggg acgatcatca ctcagctgag    660
ctctggacgg tgttatgtcc cctcatgcct gaaagctgcc actcaaggcg ttgtggaaaa    720
ccagtgccag cacatcaagc tggcggtgaa ctgccaggca gaggccaccc ctctgaccct    780
gaagagctcg gtcctgaatg caatgcaggc ctccccggaa accaaacaga ccatctggca    840
gttggccacg gaacccacag gtcctctggt gcagagaatt actaaaaaca tcttggtggt    900
gaaatgcaag gcaagccaga agcacagttt ggggtatttg catacatctt ttgtgcagaa    960
agtcagtggc aaaagcttgc ctgagcgccg cttcttctgc tcctgtcaga ctctgaaatc   1020
gcacaagtca aatgcctcca aggatgagac agcccagaga tgcattcatt tctttgcttg   1080
catctgtgcc tttgccagtg atgagacact ggctcaggaa ttctcagact tcctaaattt   1140
```

```
tgattccagc ggtcttaaag agattattgt accccagtta ggttgccatt cagaatcaac    1200
agtatctgct tgtgagtcta ctgcctctaa gtcaaagaag aggagaaagg atgaagtatc    1260
tggtgcacag atgaacagtt cactactgcc tcaagatgca gtgagcagta atctaaggaa    1320
aagtggcctg aaaaagcctg tggttgcttc ctcgttaaaa aggcaggcct gtggtcagct    1380
gttagatgag gcacaagtga ctttatcctt ccaagactgg ctggccagtg tcacagaacg    1440
catccatcaa accatgcact atcagtttga tggcaaacca gaaccattgg tgttccacat    1500
tcctcagtca ttttttgatg ccctgcaaca aagaatatct ataggaagtg caaaaaaacg    1560
gctccccaac tccaccacag cttttgttcg gaaagatgcc ttgccactgg aacctttttc    1620
caagtatact tggcatatca ctaatatcct gcaagttaaa caaatcttag ataccccaga    1680
gatgcccttg gaaatcaccc gtagctttat ccagaaccga gatgggactt atgagctatt    1740
taaatgccct aaagtggaag tagaaagcat agcagaaacc tacggtcgta tagaaaaaca    1800
accagtgctg cgaccccttgg aactaaaaac ttttctcaaa gttggcaaca cttcccccaga    1860 tcaaaaggag ccaacacctt tcatcatcga gtggatccca gatatccttc cccaatctaa    1920
gattggcgag ctgcggatca agtttgagta tggccaccac cggaatgggc atgtggcgga    1980
gtaccaagac cagcggcccc ccttggacca gcccttggaa ctggcccctc tgaccactat    2040
tactttccct aaagcaaaa caagataata atctttttgct gcttaatttg cacatcccca    2100
ccccttgaca actttaaatg ctagttaggc acttagatgg ccctgttcct tggtaaactg    2160
ctcttagcta agatgcaaat tctcagtgct ttcaagtgga ttctgttgaa gaaaatctct    2220
tgtaaatagc cttttgatg ctgctgtgta cagtcttcat tatgcattgg gcagtatttc    2280
tggctagagt tttaaaagga acagaaagaa aaccagctta ttttccttct tacggactca    2340
tctttagcgt ttatttcaac cttttgctaa ttctctgaga aatctgcagc actcagccat    2400
acaccaacag tgttggaaag ttaacaccct ggttagggca gaatgttaaa gaccatcttg    2460
gcagagttcc agccacgctc tttattctgt tctcaaataa agcagtgtca ctagtttttc    2520
ctaaaaaaaa aaaaaaaaa                                                 2540
```

<210> SEQ ID NO 4
<211> LENGTH: 5260
<212> TYPE: DNA
<213> ORGANISM: Homo sapiens

<400> SEQUENCE: 4

```
ggacccgcct cagccaatcc gctgctgccg gcgtcgggtg cgctcggcct cgcccgcggc      60
cctccttccc cggctcccgc tcgccgctcg ttcactccac cgccgccgcc gccgccgccg     120
ctgccgctgc cgctgccgca cctccgtagc tgactcggta ctctctgaag atggcagaag     180
ctcaccaagc tgtggccttt cagttcacgg tcactccgga cgggattgac ctgcggctga     240
gccatgaagc tcttagacaa atctatctct ctggacttca ttcctggaaa aagaagttca     300
tcagattcaa gaacggcatc atcactggcg tgtacccggc aagcccctcc agttggctta     360
tcgtggtggt gggcgtgatg acaacgatgt acgccaagat cgacccctcg ttaggaataa     420
ttgcaaaaat caatcggact ctggaaacgg ccaactgcat gtccagccag acgaagaacg     480
tggtcagcgg cgtgctgttt ggcaccggcc tgtgggtggc cctcatcgtc accatgcgct     540
actccctgaa agtgctgctc tcctaccacg ggtggatgtt cactgagcac ggcaagatga     600
gtcgtgccac caagatctgg atgggtatgg tcaagatctt tcaggccga aaacccatgt     660 tgtacagctt ccagacatcg ctgcctcgcc tgccggtccc ggctgtcaaa gacactgtga     720
```

```
acaggtatct acagtcggtg aggcctctta tgaaggaaga agacttcaaa cggatgacag      780
cacttgctca agattttgct gtcggtcttg gaccaagatt acagtggtat ttgaagttaa      840
aatcctggtg ggctacaaat tacgtgagcg actggtggga ggagtacatc tacctccgag      900
gacgagggcc gctcatggtg aacagcaact attatgccat ggatctgctg tatatccttc      960
caactcacat tcaggcagca agagccggca acgccatcca tgccatcctg ctttacaggc     1020
gcaaactgga ccgggaggaa atcaaaccaa ttcgtctttt gggatccacg attccactct     1080
gctccgctca gtgggagcgg atgtttaata cttcccggat cccaggagag agacagaca     1140 ccatccagca catgagagac agcaagcaca tcgtcgtgta ccatcgagga cgctacttca     1200
aggtctggct ctaccatgat gggcggctgc tgaagccccg ggagatggag cagcagatgc     1260
agaggatcct ggacaatacc tcggagcctc agcccgggga ggccaggctg gcagccctca     1320
ccgcaggaga cagagttccc tgggccaggt gtcgtcaggc ctattttgga cgtgggaaaa     1380
ataagcagtc tcttgatgct gtggagaaag cagcgttctt cgtgacgtta gatgaaactg     1440
aagaaggata cagaagtgaa gacccggata cgtcaatgga cagctacgcc aaatctctac     1500
tacacggccg atgttacgac aggtggtttg acaagtcgtt cacgtttgtt gtcttcaaaa     1560
acgggaagat gggcctcaac gctgaacact cctgggcaga tgcgccgatc gtggcccacc     1620
tttgggagta cgtcatgtcc attgacagcc tccagctggg ctatgcggag gatgggcact     1680
gcaaaggcga catcaatccg aacattccgt accccaccag gctgcagtgg gacatcccgg     1740
gggaatgtca agaggttata gagacctccc tgaacaccgc aaatcttctg gcaaacgacg     1800
tggatttcca ttccttccca ttcgtagcct ttggtaaagg aatcatcaag aaatgtcgca     1860
cgagcccaga cgccttttgtg cagctggccc tccagctggc gcactacaag gacatgggca     1920
agttttgcct cacatacgag gcctccatga cccggctctt ccgagagggg aggacggaga     1980
ccgtgcgctc ctgcaccact gagtcatgcg acttcgtgcg ggccatggtg gacccggccc     2040
agacggtgga acagaggctg aagttgttca agttggcgtc tgagaagcat cagcatatgt     2100
atcgcctcgc catgaccggc tctgggatcg atcgtcacct cttctgcctt tacgtggtgt     2160
ctaaatatct cgctgtggag tcccctttcc ttaaggaagt tttatctgag ccttggagat     2220
tatcaacaag ccagacccct cagcagcaag tggagctgtt tgacttggag aataacccag     2280
agtacgtgtc cagcggaggg ggcttttggac cggttgctga tgacggctat ggtgtgtcgt     2340
acatccttgt gggagagaac ctcatcaatt tccacatttc ttccaagttc tcttgccctg     2400
agacggattc tcatcgcttt ggaaggcacc tgaaagaagc aatgactgac atcatcactt     2460
tgtttggtct cagttctaat tccaaaaagt aattccactg gagctgctgg gaaggaaaac     2520
gagctcttct gatgcaaacc aaatgaaaaa taggcattaa tcctgacctt agctcgggat     2580
gaaacactgc tcttaaaaaa actcagtttt ccttccagaa aatgtgggtg tttttttttc     2640
ctagaacagt atctctcccc tgtgaagcat aaccccacta cttccagact gccctccct     2700 tggggggacat ctgataaagt ctcccctgat gtctccgcat cggcttggat ttattaaggg     2760
atgcaaatct tgttgagtta atgaaggaat tagtagggtt gtggcttcac acacagtgga     2820
atggaaatgg tgtgctttct cagtggcaac cgaaggccta gtgcttaagg gcatttagca     2880
tcatccaagc agggtaaact tttgttttgt taaaagaaaa atgtgttatt caagttggtg     2940
tccccagttg tagctaacac atctggaatg cactaaccaa aatgctgtgc tttgagacc     3000 tgcttttgtc accgtgggta accgttcccg tctggtccag tagcctgtgt ttgcctctcc     3060
```

```
acatttgaag caagcaggat gcaaggtctt cagtttact gaccttgtat gtcttcaagt    3120
cttcacaacc cagtgcctta aaaatgaaag gccctaaatg taagggagat ggagagaaag    3180
atttattttg tagagtcttt gggtggaatt gtgggtatac tgttccctc acaattgact    3240
gagtatggat aaccgtacat aagcatttgc tacaccccac cagcccctc ccctcagaa    3300
acaccagttc cttcccaagg gcagctgtgc cagactcccc tcccgggact gccttcttgt    3360
catcataagc aacaaaagaa ataacaggca catgtcataa aagggagca agggccgtga    3420
tggtcagata attcactcaa gaataaaaca tgacacgtgc ctcaggagga tctctttccc    3480
aaagtgacag caaggagggc agggcatcgg ccaccaagcg gggactagca agtgaggaag    3540
gggagggcag cccaccgtgg tgaggagaga gtggctccac gaccccaagg gatggccttc    3600
tcctcccacc cggtgagggg aaagactcac cagagggtga tggagacagt atgccggctc    3660
accttggtga ccagccaaga tgtctcaagt gacagtgcta ggtgttcacc cagcctgtcc    3720
ttcagatagg agtgccttca cgaaagcgtc tcatggacca caaagcaatt atgcactgag    3780
tcatcttcag tatttaatgc aaaaatgaag catcatggaa tgaaattccc actgtctgtc    3840
atgacaagct tagctgtcca ttgttttaaa ttgtgtattt attttttttga ccacttggtt    3900
ctagttgggc ctgactcctt cagagtgctg caccccgata gtacaacagc gatggctgaa    3960
ctgttggagt cgatggaagg tgcttgccgg agaacacgtg ccttttttt ttttttttt    4020
tttgagatgg agtttcactc ttgttgccca ggctggagtg cagtggtgca atctcggctc    4080
actgcagcat ctgccttgca ggttcaagcg attctcctgt ctcagcctcc caagtagctg    4140
ggattacacg cccaacacca tgccctgcta atttttgtat ttttagtaga cgggggttt    4200
catcatattg gtcaggctgg tctcgaactc ctgacctcag gtgatccacc tgcctcagcc    4260
tcccaaagtg ctgggattac aggcatgagc accatgcgc ggcccacatg catgttttat    4320
gtatgtatac ttcatgatgt aaaaatccca cctttatggg ccaaagatttt ttttctcct    4380
gaaagcaaga aaaatgaaa acaaaagaca aaaaaaaaa aaaagcgtc caggcgcggt    4440
ggctcatgcg tgtaatccca gcactttggg aggccaaggc gggcggatca cgaggtcagg    4500
agatggagac catcctggct aacacggtga accccgtctc tactaaaaa ttcaaaaat    4560
gagccgggcg tggtggcggg cgcctgtagt cccagctact caggaggctg aggcaggaga    4620
atggcgtgaa cccgggaggc ggagcttgca gtgagccgag atcgctccac tgcactccag    4680
cctgggcgac agagcgagac tccgtctaaa aaaaaagca aaacaaacc aacaacaaaa    4740
gccctgact gtccgtcaag caggcagcgg ggatgtagct ctctctgccc tgggcaagaa    4800
tagcacttcc cgttaaaagc cagcagccgg cgtcagtccc tatcagagcc agctagatca    4860
tgcactgttg accactgagc aatctgtgtt acactagagt tcacagggca ttttgagtgt    4920
agacgtgagt gcttaaacat atttgggttt ctctctcagg ttttaaatgt ttcaaatgta    4980
attgttgctc atcagtgcag ttatcaatgc aattttatat tccttgaggg gagaaagagg    5040
ggtcttattg tacatgtcca aggggggtga taagagtatt atctgtttaa tttaattgga    5100
acaaaccatt gtcttaacgc agccatggtt tgaatttgtt atcttgggct gaccggtgca    5160
tgtaaataca gtatgctctt tggatgtaaa tcttagaaat gcagtgtgaa tgtaggttat    5220
cattaataaa acattaaccc cagtctacta caaaaaaaaa                        5260
```

<210> SEQ ID NO 5
<211> LENGTH: 1647
<212> TYPE: DNA
<213> ORGANISM: Homo sapiens

<400> SEQUENCE: 5

```
gaagatccaa gcaggcggag ccgcggtctg gtccgcgggg taggcggggc gcaagagtgt    60
tcccgggggc gggggggccga cccgcgtcta aaggtttccg cgattcaccc gccggcgcct   120
ggcctggccc agttgcacca cgagcgctgc ggacactcgg ggcggcagtc ggtctgtcag   180
tcctcccgcc aggtcccgcg gcccgcacct gccgcccgca cctgcagctc cgcacctgcg   240
gccagtgcct actgccctct cttgccgccc gcacctgcag ccccgcacct gccgcttgca   300
cctgcagccc cgcgctctac ccggttcaag catggctgac caggcgccct cgacacgga   360
cgtcaacacc ctgacccgct tcgtcatgga ggagggcagg aaggcccgcg cacgggcga   420
gttgacccag ctgctcaact cgctctgcac agcagtcaaa gccatctctt cggcggtgcg   480
caaggcgggc atcgcgcacc tctatggcat tgctggttct accaacgtga caggtgatca   540
agttaagaag ctggacgtcc tctccaacga cctggttatg aacatgttaa agtcatcctt   600
tgccacgtgt gttctcgtgt cagaagaaga taaacacgcc atcatagtgg aaccggagaa   660
aaggggtaaa tatgtggtct gttttgatcc ccttgatgga tcttccaaca tcgattgcct   720
tgtgtccgtt ggaaccattt ttggcatcta tagaaagaaa tcaactgatg agccttctga   780
gaaggatgct ctgcaaccag gccggaacct ggtggcagcc ggctacgcac tgtatggcag   840
tgccaccatg ctggtccttg ccatggactg tggggtcaac tgcttcatgc tggacccggc   900
catcggggag ttcattttgg tggacaagga tgtgaagata aaaagaaag gtaaaatcta   960
cagcccttaac gagggctacg ccagggactt tgaccctgcc gtcactgagt acatccagag  1020
gaagaagttc cccccagata attcagctcc ttatggggcc cggtatgtgg gctccatggt  1080
ggctgatgtt catcgcactc tggtctacgg agggatattt ctgtaccccg ctaacaagaa  1140
gagccccaat ggaaagctga gactgctgta cgaatgcaac cccatggcct acgtcatgga  1200
gaaggctggg ggaatggcca ccactgggaa ggaggccgtg ttagacgtca ttcccacaga  1260
cattcaccag agggcgccgg tgatcttggg atccccgac gacgtgctcg agttcctgaa  1320
ggtgtatgag aagcactctg cccagtgagc acctgccctg cctgcatccg gagaattgcc  1380
tctacctgga cctttttgtct cacacagcag taccctgacc tgctgtgcac cttacattcc  1440
tagagagcag aaataaaaag catgactatt ccaccatca aatgctgtag aatgcttggc  1500
actccctaac caaatgctgt ctccataatg ccactggtgt taagatatat tttgagtgga  1560
tggaggagaa ataaacttat tcctccttaa aaaaaaaaa aaaaaaaaa aaaaaaaaa  1620
aaaaaaaaaa aaaaaaaaaa aaaaaaa                                      1647
```

<210> SEQ ID NO 6
<211> LENGTH: 2240
<212> TYPE: DNA
<213> ORGANISM: Homo sapiens

<400> SEQUENCE: 6

```
gagtcagagc ctcttctctc taagtcacgg gaactgccct tgctacttgt gacctgccct    60
ttactcagca gttttttgttc tgggaagccc tgggattctg ctaataccta tcactgtagg   120
tgctgaaggg aaacagatga agaacatgac ctcaaggagc ttcctgtcaa tgagaagacc   180
aagctgacgc ctggcaaaga tattaaagag agcctgaaaa ctgttccttg gacatcttat   240
gaatgtcaga aaataccttt tggagggtta agatcagg ggacatggtt gttcacattt   300
gctgccacgg aacaccgcca gtcttcactt ggaaacagaa tcacgccttg tgaagagatc   360
```

| | |
|---|---|
| atccctaagc aggagagaag ctactaaagg attgtgtcct cctccacctt ccctgtgctc | 420 |
| ggtctccacc tgtctcccat tctgtgacga tggttcaatg aagagactc tgccagctgc | 480 |
| attacttgtg ggctctgggc tgctatatgc tgctggccac tgtggctctg aaactttctt | 540 |
| tcaggttgaa gtgtgactct gaccacttgg gtctggagtc cagggaatct caaagccagt | 600 |
| actgtaggaa tatcttgtat aatttcctga aacttccagc aaagaggtct atcaactgtt | 660 |
| caggggtcac ccgaggggac caagaggcag tgcttcaggc tattctgaat aacctggagg | 720 |
| tcaagaagaa gcgagagcct ttcacagaca cccactacct ctccctcacc agagactgtg | 780 |
| agcacttcaa ggctgaaagg aagttcatac agttcccact gagcaaagaa gaggtggagt | 840 |
| tccctattgc atactctatg gtgattcatg agaagattga aactttgaa aggctactgc | 900 |
| gagctgtgta tgcccctcag aacatatact gtgtccatgt ggatgagaag tccccagaaa | 960 |
| cttcaaaga ggcggtcaaa gcaattattt cttgcttccc aaatgtcttc atagccagta | 1020 |
| agctggttcg ggtggtttat gcctcctggt ccagggtgca agctgacctc aactgcatgg | 1080 |
| aagacttgct ccagagctca gtgccgtgga atacttcct gaatacatgt gggacggact | 1140 |
| ttcctataaa gagcaatgca gagatggtcc aggctctcaa gatgttgaat gggaggaata | 1200 |
| gcatggagtc agaggtacct cctaagcaca agaaacccg ctggaaatat cactttgagg | 1260 |
| tagtgagaga cacattacac ctaaccaaca agaagaagga tcctcccct tataatttaa | 1320 |
| ctatgtttac agggaatgcg tacattgtgg cttcccgaga tttcgtccaa catgttttga | 1380 |
| agaaccctaa atcccaacaa ctgattgaat gggtaaaaga cacttatagc ccagatgaac | 1440 |
| acctctgggc caccctcag cgtgcacggt ggatgcctgg ctctgttccc aaccaccca | 1500 |
| agtacgacat ctcagacatg acttctattg ccaggctggt caagtggcag ggtcatgagg | 1560 |
| gagacatcga taagggtgct ccttatgctc cctgctctgg aatccaccag cgggctatct | 1620 |
| gcgtttatgg ggctggggac ttgaattgga tgcttcaaaa ccatcacctg ttggccaaca | 1680 |
| agtttgaccc aaaggtagat gataatgctc ttcagtgctt agaagaatac ctacgttata | 1740 |
| aggccatcta tgggactgaa ctttgagaca cactatgaga gcgttgctac ctgtggggca | 1800 |
| agagcatgta caaacatgct cagaacttgc tgggacagtg tgggtgggag accagggctt | 1860 |
| tgcaattcgt ggcatccttt aggataagag ggctgctatt agagtgtggg taagtagatc | 1920 |
| ttttgccttg caaattgctg cctgggtgaa tgctgcttgt tctctcaccc ctaaccctag | 1980 |
| tagttcctcc actaactttc tcactaagtg agaatgagaa ctgctgtgat agggagagtg | 2040 |
| aaggagggat atgtggtaga gcacttgatt tcagttgaat gcctgctggt agcttttcca | 2100 |
| ttctgtggag ctgccgttcc taataattcc aggtttggta gcgtggagga gaactttgat | 2160 |
| ggaaagagaa ccttccctc tgtactgtta acttaaaaat aaatagctcc tgattcaaag | 2220 |
| taaaaaaaaa aaaaaaaaa | 2240 |

<210> SEQ ID NO 7
<211> LENGTH: 2384
<212> TYPE: DNA
<213> ORGANISM: Homo sapiens

<400> SEQUENCE: 7

| | |
|---|---|
| atctgccacc gcagtctggt tggagctgtt gtcttgtatg ctcagcgagg cccggagaga | 60 |
| cccgggagag agctaggccg agtccaccgc ccgagtctgc tgcccgagcc gcgttacgc | 120 |
| acaaagccgc cgatccccgg cctggggtga gcagagcgac caccgccggg agcagcgcg | 180 |
| gcgagacgca cggtgcgccc tatgccccg cgccccacc gccccgccg cggcagccga | 240 |

```
agcgcagcga gagaacgcgc caccgcgggg cccgggtgca gctagcgacc ctctcgccac    300
ctgcgcgcag cccgaggtga gcagtgagcg gcgagcggga gggcagcgag gcgttcgcgg    360 gcccctcct gctgcccggg cccggcccgc tcatggcggc catccgcaag aagctggtgg     420
tggtgggcga cggcgcgtgt ggcaagacgt gcctgctgat cgtgttcagt aaggacgagt    480
tccccgaggt gtacgtgccc accgtcttcg agaactatgt ggccgacatt gaggtggacg    540
gcaagcaggt ggagctggcg ctgtgggaca cggcgggcca ggaggactac gaccgcctgc    600
ggccgctctc ctacccggac accgacgtca ttctcatgtg cttctcggtg gacagcccgg    660
actcgctgga gaacatcccc gagaagtggg tccccgaggt gaagcacttc tgtcccaatg    720
tgcccatcat cctggtggcc aacaaaaaag acctgcgcag cgacgagcat gtccgcacag    780
agctggcccg catgaagcag gaacccgtgc gcacggatga cggccgcgcc atggccgtgc    840
gcatccaagc ctacgactac ctcgagtgct ctgccaagac caaggaaggc gtgcgcgagg    900
tcttcgagac ggccacgcgc gccgcgctgc agaagcgcta cggctcccag aacggctgca    960
tcaactgctg caaggtgcta tgagggccgc gcccgtcgcg cctgcccctg ccggcacggc   1020
tccccctcct ggaccagtcc cccgcgagcc cggagaaggg gagacccgtg tcccacaagg   1080
accccaccgg cctgcctggc atctgtctgc tgacgcctct ggcttgcgcc aggacttggc   1140
gtgggcaccg ggcgccccca tcccagtgtc tgtgtgcgtc cagctgtgtt gcacaggcct   1200
gggctcccca ctgagtgcca agggtcccct gagcatgctt ttctgaagag ccgggcctca   1260
gagtgtgtgg ctgtgtgtct gttcgactcc cctcgcccca ttttcacccc accccgcct    1320 ctgatccccg ggggcgagat tggcgcggga gtgtggccgc gccccatcag atgttctccc   1380
ttcaccagcg ggagcttgat atcccttgtc tgtaacatag accccgggta ctgcgggagg   1440
ggagggctgc tggggaggat gggggatgt tatataaata tagatataat tttattttcg    1500
gagctaagat ggtgttattt aagggtggtg atgggtgagc gctctggccc aggctgggcc   1560
agactcccgc ccaagcatga acaggacttg accatctttc caacccctgg ggaagacatt   1620
tgcaactgac ttggggagga cacagcttca gcacagcctc tcctgcgggc cagcccgctg   1680
cgaaccctcc accagctacc ggagggagga gggaggatgc gctgtggggt tgttttgcc    1740 ataagcgaac tttgtgcctg tcctagaagt gaaaattgtt cagtccaaga aactgatgtt   1800
atttgattta tttaaaggct aaaatttgtt tttttattct ttgcacaatt gtttcattgt   1860
ttgacactta atgcactcgt catttgcata cgacagtagc attctgacca cacttgtacg   1920
ctgtaacctc atctacttct gatgttttta aaaaatgact tttaacaagg agagggaaaa   1980
gaaacccact aaattttgct ttgtttcctt gaagaatgtg gcaacactgt tttgtgattt   2040
tatttgtgca ggtcatgcac acagttttga taaagggcag taacaagtat tggggcctat   2100
tttttttttt tccacaaggc attctctaaa gctatgtgaa attttctctg cacctctgta   2160
cagagaatac acctgcccct gtatatcctt ttttcccctc ccctccctcc cagtggtact   2220
tctactaaat tgttgtcttg tttttttattt tttaaataaa ctgacaaatg acaaaatggt   2280
gagcttatga tgtttacata aaagttctat aagctgtgta tacagttttt tatgtaaaat   2340
attaaaagac tatgatgatg acatttaaaa aaaaaaaaaa aaaa                    2384
```

<210> SEQ ID NO 8
<211> LENGTH: 3261
<212> TYPE: DNA
<213> ORGANISM: Homo sapiens

```
<400> SEQUENCE: 8
gcttggaagc cagcgctgcg ctccccgtgg gaagcgatcg tctcctctgt caactcgcgc      60
ctgggcactt agcccctccc gtttcagggc gccgcctccc cggatggcaa acactataaa     120
gtggcggcga ataaggttcc tcctgctgct ctcggtttag tccaagatca gcgatatcac     180 gcgtccccg gagcatcgcg tgcaggagcc atggcgcggg agctatacca cgaagagttc      240
gcccgggcgg gcaagcaggc ggggctgcag gtctggagga ttgagaagct ggagctggtg     300
cccgtgcccc agagcgctca cggcgacttc tacgtcgggg atgcctacct ggtgctgcac     360
acggccaaga cgagccgagg cttcacctac cacctgcact tctggctcgg aaaggagtgt     420
tcccaggatg aaagcacagc tgctgccatc ttcactgttc agatggatga ctatttgggt     480
ggcaagccag tgcagaatag agaacttcaa ggatatgagt ctaatgactt tgttagctat     540
ttcaaaggcg gtctgaaata caaggctgga ggcgtggcat ctggattaaa tcatgttctt     600
acgaacgacc tgacagccaa gaggctccta catgtgaagg tcgtagagt ggtgagagcc      660 acagaagttc cccttagctg ggacagtttc aacaagggtg actgcttcat cattgacctt    720
ggcaccgaaa tttatcagtg gtgtggttcc tcgtgcaaca aatatgaacg tctgaaggca    780
aaccaggtag ctactggcat tcggtacaat gaaaggaaag aaggtctga actaattgtc      840 gtggaagaag aagtgaacc ctcagaactt ataaaggtct taggggaaaa gccagagctt      900
ccagatggag gtgatgatga tgacattata gcagacataa gtaacaggaa aatggctaaa    960
ctatacatgg tttcagatgc aagtggctcc atgagagtga ctgtggtggc agaagaaaac   1020
cccttctcaa tggcaatgct gctgtctgaa gaatgcttta ttttggacca cggggctgcc   1080
aaacaaattt tcgtatggaa aggtaaagat gctaatcccc aagagaggaa ggctgcaatg   1140
aagacagctg aagaatttct acagcaaatg aattattcca agaataccca aattcaagtt    1200
cttccagaag gaggtgaaac accaatcttc aaacagtttt ttaaggactg gagagataaa   1260
gatcagagtg atggcttcgg gaaagtttat gtcacagaga agtggctca aataaaacaa    1320 attccctttg atgcctcaaa attacacagt tctccgcaga tggcagccca gcacaatatg   1380
gtggatgatg ttctggcaa agtggagatt tggcgtgtag aaaacaatgg taggatccaa    1440
gttgaccaaa actcatatgg tgaattctat ggtggtgact gctacatcat actctacacc   1500
tatcccagag acagattat ctacacgtgg caaggagcaa atgccacacg agatgagctg     1560
acaacatctg cgttcctgac tgttcagttg gatcggtccc ttggaggaca ggctgtgcag   1620
atccgagtct cccaaggcaa agagcctgtt cacctactga gtttgttcaa agacaaaccg   1680
ctcattattt acaagaatgg aacatcaaag aaaggaggtc aggcacctgc tccccctaca   1740
cgcctctttc aagtccggag aaacctggca tctatcacca gaattgtgga ggttgatgtt   1800
gatgcaaatt cactgaattc taacgatgtt tttgtcctga aactgccaca aaatagtggc   1860
tacatctggg taggaaaagg tgctagccag gaggaggaga aaggagcaga gtatgtagca   1920
agtgtcctaa agtgcaaaac cttaaggatc caagaaggcg aggagccaga ggagttctgg   1980
aattcccttg gagggaaaaa agactaccag acctcaccac tactggaaac ccaggctgaa   2040
gaccatccac ctcggcttta cggctgctct aacaaaactg gaagatttgt tattgaagag   2100
attccaggag agttcacccca ggatgattta gctgaagatg atgtcatgtt actagatgct   2160
tgggaacaga tatttatttg gattggcaaa gatgctaatg aagttgagaa aaagaatct    2220 ctgaagtctg ccaaaatgta ccttgagaca gaccttctg gaagagacaa gaggacacca    2280
attgtcatca taaaacaggg ccatgagcca cccacattca caggctggtt cctgggctgg   2340
```

```
gattccagca agtggtaaat tggtatttgt aaaaagcaaa caaacattac aaggcagtta    2400
tctcattgct gttttgggag aggaacggga aaagcttttt gcttatttgt cttttgaaaa    2460
ttaaggctgg gcgcggtggc tcacacctgt aatcccagca ctttgagagg atgaggtagg    2520
cggatcactg gggtcaggat ttcgagacca gcctggccaa catggcgaaa cctcgcctct    2580
actaaaaata caaaaaaatt agctgcgcgt ggtggtgcac gcctgtagtc cctgctactt    2640
ggaaggctga gacaggaaaa ttgcttgaac ccaggaggct gaggttgcag tgagccagga    2700
ttgcgccacc acactccagc ctgggcaaca gagactctgt ctcaaaaaaa aaaaaaaaa     2760 aaattaacct caaccaaacg cctattttt aatgcttagt tttggcttga aattcttctt    2820
cacctggagt tttcttacgt aatacatta aaataacctg aaggaaactt tcgttatggg     2880
ccaatattag ctcttatgga aactgattta tatcttttt atgacctttc aaaagtaaaa    2940
tactatgcat aatctagaaa gatttgtcag ataggaaatt ttataatgca ttagccatta    3000
gtcagagttg tttttaaca tgccagagaa aaagttgtaa tgccttggaa gttattctct     3060
tttctataga ttgtgttcaa aagatgtgta tacttgcaat aaggtttatg ttaaggtggc    3120
tttaacaatt ggttgctatt ttccttcttt agtcaatatg actttgatgt cattaactgc    3180
taagtgttat tttctaagag gaattttatc ttttttttaa ccttattaaa agcctttgaa    3240
aacacaaaaa aaaaaaaaaa a                                              3261

<210> SEQ ID NO 9
<211> LENGTH: 4795
<212> TYPE: DNA
<213> ORGANISM: Homo sapiens

<400> SEQUENCE: 9
agctgagcaa cccgaaccga gaggtgcccg cgaaactgca ggcggcggca gcggcagcaa      60
aagagaagga aaaatctcca gctggatacg aagctccaga atcctggcca taggctcaga    120
acttttacag gtcgcgctgc aatgggcccc cacttcgctc ctaagtcctc acgcagcaca    180
gggctttgcc tttccctgcg gaggaaggag aaataggagt tgcaggcagc agcaggtgca    240
taaatgcggg ggatctcttg cttcctagaa ctgtgaccgg tggaatttct ttccctttt     300 cagtttaccg caagagagat gctgtctcca gacttctgaa ctcaaacgtc tcctgaagct    360
tgaaagtgga ggaattcaga gccaccgcgg gcaggcgggc agtgcatcca gaagcgttta    420
tattctgagc gccagttcag cttcaaaaa gagtgctgcc cagaaaaagc cttccaccct    480
cctgtctggc tttagaagga ccctgagccc caggcgccag ccacaggact ctgctgcaga    540 gggggggttgt gtacagatag tagggctta ccgcctagct tcgaaatgga taacgtcctc    600
ccggtggact cagacctctc cccaaacatc tccactaaca cctcggaacc caatcagttc    660
gtgcaaccag cctggcaaat tgtccttttgg gcagctgcct acacggtcat tgtggtgacc    720
tctgtggtgg gcaacgtggt agtgatgtgg atcatcttag cccacaaaag aatgaggaca    780
gtgacgaact attttctggt gaacctggcc ttcgcggagg cctccatggc tgcattcaat    840
acagtggtga acttcaccta tgctgtccac aacgaatggt actacggcct gttctactgc    900
aagttccaca cttctttcc catcgccgct gtcttcgcca gtatctactc catgacggct    960 gtggccttg ataggtacat ggccatcata catccctcc agcccggct gtcagccaca     1020 gccaccaaag tggtcatctg tgtcatctgg gtcctggctc tcctgctggc cttcccccag    1080
ggctactact caaccacaga gaccatgccc agcagagtcg tgtgcatgat cgaatggcca    1140
```

```
gagcatccga acaagattta tgagaaagtg taccacatct gtgtgactgt gctgatctac    1200
ttcctccccc tgctggtgat tggctatgca tacaccgtag tgggaatcac actatgggcc    1260
agtgagatcc ccggggactc ctctgaccgc taccacgagc aagtctctgc caagcgcaag    1320
gtggtcaaaa tgatgattgt cgtggtgtgc accttcgcca tctgctggct gcccttccac    1380
atcttcttcc tcctgcccta catcaaccca gatctctacc tgaagaagtt tatccagcag    1440
gtctacctgg ccatcatgtg gctggccatg agctccacca tgtacaaccc catcatctac    1500
tgctgcctca atgacaggtt ccgtctgggc ttcaagcatg ccttccggtg ctgcccttc     1560 atcagcgccg cgactatga ggggctggaa atgaaatcca cccggtatct ccagacccag    1620
ggcagtgtgt acaaagtcag ccgcctggag accaccatct ccacagtggt gggggcccac    1680
gaggaggagc cagaggacgg ccccaaggcc cacccctcgt ccctggacct gacctccaac    1740
tgctcttcac gaagtgactc caagaccatg acagagagct tcagcttctc ctccaatgtg    1800
ctctcctagg ccacagggcc tttggcaggt gcagccccca ctgcctttga cctgcctccc    1860
ttcatgcatg gaaattccct tcatctggaa ccatcagaaa cacctcaca ctgggacttg      1920 caaaaagggt cagtatgggt tagggaaaac attccatcct tgagtcaaaa aatctcaatt    1980 cttcccctatc tttgccaccc tcatgctgtg tgactcaaac caaatcactg aactttgctg    2040
agcctgtaaa ataaaggtc ggaccagctt ttcccaaaag cccattcatt ccattctgga     2100
agtgactttg gctgcatgcg agtgctcatt tcaggatgaa ttctgcagca cagctgcgga    2160
cccggaagac tcattttcct ggagccccgt gttacttcaa taaagttatc tcagattagc    2220
ctcctgcagc tggaggctcc tatcacccca gcctacgctt gacagggtga acaaaagaag    2280
gcaccacata acatctaaat gaaaaattta gccctgtctt ctaagcatct gtgaaaagaa    2340
acatatgtat tcccctttt ggcatctcag tatttcagta catttataca tcatgagatt    2400
gagaacctcg ggcttccaca ttatgtcccc ggtgactgtc ctgagcagcc gacgcaagca    2460
gaatatgtcc actgatacct gctagttctc ttacagacca ggaattggga gacttgcact    2520
acatttaatg tgtagttgac cctctttttcc tacttgtaaa caaggggact gaactagata    2580
atctaagtgt tccttcgaat cttaacatcc cgtggttcaa ggattgtatg agttttttgt    2640 ttgtttttaca aaaaaaaaca aaacgaagaa taaaagaata gaaaagaata ggagcagtga    2700
gtcttgtaac taatacccag ttcctggaga tgtagcaact gctaaggcca tctgtaacta    2760
tccatctcag acattctccg atttatctta aaatcctgag tacattcctt ctcatggaag    2820
gttttggctt ttgacagagc agaggacttc atgccaaggc ctgcatccat ccagctttag    2880
caggcagaat tcatagctg cagaacactg tcagagaaga caaatgtggg ctccctgctt     2940
taaccttttg ggtattttag ggtgggggcc ctaaccttca ttcttagttt tacactagca    3000
tcgtgctcat atgtgcgaca agcaagaagg ctgcactttg cagctgcact tctgggaaga    3060
gggcatcttg catcttccct tcagactctc tgaatgtctc ctccctgctc catggctttg    3120
ccagcttcct gtctctaagg ggtagaatga ctcatcaacc ctaaaggaca gtcagtcttc    3180
caagagccat gaactgaatg ctttatatcc taatttagat ttagagtttc cagaaggtga    3240
gcatgcagtt ttgttttgtt ttttttctg tctcccaaat ctgtgttttt tccagatatg     3300
gctggaagca gaagcttcat gtaacatcca tgaatgtcct cctggtagtt tgcataatgg    3360
atgcacatgt gccgcatcca taacattaag gggagaataa tgcatggttt acagcctttg    3420
ccagccctgc tggctctaat tctaccaggg catccacagg cctgggggaa gagaaacag     3480 tataagccag aaaacctcaa gaactacatt ctctaaagca gcatggaaag ttttaaataa    3540
```

```
actaagtgaa gccagatcat tgcagatata taaatggaag acaaaattta gaagcaacaa    3600
aagttagtgc cctaagcatt agtcatactt ccaatagaga atcttgctgt gtatggatta    3660
ctcactttgg aagaatgtaa agagctaaca tgattatgag aagtacctga gaagatggtg    3720
tcaagaagtt ggggacaccc catctatgga agagaaggtt agagttgagc tcaacgagga    3780
ttaactgagt gcctcctctg gactttgccc tgaactggga acacacagcc cctgcagctc    3840
ttgaagagcc taccttattg gccatcacta actaactcac cagtcctagt gagtctaagc    3900
tgcccagcag tcttggaggc atctgagagg acagattctc cacagaattc taaaaaccca    3960
cactcaacat gggcagtcaa gccaaagact gggacctttg gagagcctct ggaatgagag    4020
ttctctgggg tacttccaaa gggagctggc agtcagtcca ggggacctaa aggaatttgg    4080
ttgaacagta tcatctctgt gcatagtaag agggaatgtt gggtggtccg ggcagtttcc    4140
aatatggcaa agcatctgct tggacagtgc cagcaagcct tcctctgacc cagtctccaa    4200
tgtccactaa cttataaaaa tgtcatcaac tcccacatgt aagaaacacc atgatttgta    4260
ctgtgcatgg gtcacattct tattctagaa atgcatcacc ctgtgtttat ccaagtgtgt    4320
ttacttggtg taatgtccag tagtaataga atatgaaata tcaaggaacc atctttgtta    4380
cgtgacttcc aaaatgtgag atctcattgc tgtcactgtg atatttgtat tgtgtgaatc    4440
tcttcctcct cttcctcctc atgctttctc agggaggagc cctgatgtat atcatgaact    4500
cacagttcct agaccacagt aattgagggg cggtgggggg gcctttatcg agaagctag    4560 agaacaagag tccttctcct ccttatcccc caacaggaca ctaagagaca aggactgagt    4620
ggaatcctgg agaaagggga ctcaggaact gacctcattg gcctgatttg tgaggagagg    4680
agtataagtg gagaggggcc attcctgagg tttccgtgtt ttccagcctg gtctcctgga    4740
aagaatcttt atacagaaat aaagtatgtg tttcactcaa aaaaaaaaa aaaaa          4795

<210> SEQ ID NO 10
<211> LENGTH: 1439
<212> TYPE: DNA
<213> ORGANISM: Homo sapiens

<400> SEQUENCE: 10
agtcacattt cagccactgc tctgagaatt tgtgagcagc ccctaacagg ctgttacttc      60
actacaactg acgatatgat catcttaatt tacttatttc tcttgctatg ggaagacact     120
caaggatggg gattcaagga tggaatttt cataactcca tatggcttga acgagcagcc     180
ggtgtgtacc acagagaagc acggtctggc aaatacaagc tcacctacgc agaagctaag     240
gcggtgtgtg aatttgaagg cggccatctc gcaacttaca agcagctaga ggcagccaga     300
aaaattggat tcatgtctg tgctgctgga tggatggcta agggcagagt tggataccc       360 attgtgaagc cagggcccaa ctgtggattt ggaaaaactg gcattattga ttatggaatc     420
cgtctcaata ggagtgaaag atgggatgcc tattgctaca acccacacgc aaaggagtgt     480
ggtggcgtct ttacagatcc aaagcaaatt tttaaatctc caggcttccc aaatgagtac     540
gaagataacc aaatctgcta ctggcacatt agactcaagt atggtcagcg tattcacctg     600
agttttttag attttgacct tgaagatgac ccaggttgct ggctgatta tgttgaaata     660 tatgacagtt acgatgatgt ccatggcttt gtgggaagat actgtggaga tgagcttcca     720
gatgacatca tcagtacagg aaatgtcatg accttgaagt ttctaagtga tgcttcagtg     780
acagctggag gtttccaaat caaatatgtt gcaatggatc ctgtatccaa atccagtcaa     840
```

```
ggaaaaaata caagtactac ttctactgga aataaaaact ttttagctgg aagatttagc    900
cacttataaa aaaaaaaaaa aggatgatca aaacacacag tgtttatgtt ggaatctttt    960
ggaactcctt tgatctcact gttattatta acatttattt attattttc taaatgtgaa    1020 agcaatacat aatttaggga aaattggaaa atataggaaa ctttaaacga gaaaatgaaa    1080
cctctcataa tcccactgca tagaaataac aagcgttaac attttcatat ttttttcttt    1140
cagtcatttt tctatttgtg gtatatgtat atatgtacct atatgtattt gcatttgaaa    1200
ttttggaatc ctgctctatg tacagttttg tattatactt tttaaatctt gaactttata    1260
aacattttct gaaatcattg attattctac aaaaacatga ttttaaacag ctgtaaaata    1320
ttctatgata tgaatgtttt atgcattatt taagcctgtc tctattgttg gaatttcagg    1380
tcattttcat aaatattgtt gcaataaata tccttgaaca cacaaaaaaa aaaaaaaaa    1439
```

<210> SEQ ID NO 11
<211> LENGTH: 19
<212> TYPE: DNA
<213> ORGANISM: artificial sequence
<220> FEATURE:
<223> OTHER INFORMATION: shRNA
<400> SEQUENCE: 11
tcttgccaag gtttatggc                                                 19

<210> SEQ ID NO 12
<211> LENGTH: 19
<212> TYPE: DNA
<213> ORGANISM: artificial sequence
<220> FEATURE:
<223> OTHER INFORMATION: shRNA
<400> SEQUENCE: 12
atctctttgg acttgaagc                                                 19

<210> SEQ ID NO 13
<211> LENGTH: 19
<212> TYPE: DNA
<213> ORGANISM: artificial sequence
<220> FEATURE:
<223> OTHER INFORMATION: shRNA
<400> SEQUENCE: 13
tgatgtctgg tgtagtagg                                                 19

<210> SEQ ID NO 14
<211> LENGTH: 21
<212> TYPE: DNA
<213> ORGANISM: artificial sequence
<220> FEATURE:
<223> OTHER INFORMATION: shRNA
<400> SEQUENCE: 14
atctcctgaa tatttcagca g                                              21

<210> SEQ ID NO 15
<211> LENGTH: 19
<212> TYPE: DNA
<213> ORGANISM: artificial sequence
<220> FEATURE:
<223> OTHER INFORMATION: shRNA
<400> SEQUENCE: 15
atgacattga tctgatcca                                                 19

```
<210> SEQ ID NO 16
<211> LENGTH: 19
<212> TYPE: DNA
<213> ORGANISM: artificial sequence
<220> FEATURE:
<223> OTHER INFORMATION: ShRNA

<400> SEQUENCE: 16
tcttcaacag aatccactt                                              19

<210> SEQ ID NO 17
<211> LENGTH: 19
<212> TYPE: DNA
<213> ORGANISM: artificial sequence
<220> FEATURE:
<223> OTHER INFORMATION: ShRNA

<400> SEQUENCE: 17
aaacgctaaa gatgagtcc                                              19

<210> SEQ ID NO 18
<211> LENGTH: 19
<212> TYPE: DNA
<213> ORGANISM: artificial sequence
<220> FEATURE:
<223> OTHER INFORMATION: ShRNA

<400> SEQUENCE: 18
attggtttga tttcctccc                                              19

<210> SEQ ID NO 19
<211> LENGTH: 21
<212> TYPE: DNA
<213> ORGANISM: artificial sequence
<220> FEATURE:
<223> OTHER INFORMATION: ShRNA

<400> SEQUENCE: 19
aacatgttca taaccaggtc g                                           21

<210> SEQ ID NO 20
<211> LENGTH: 19
<212> TYPE: DNA
<213> ORGANISM: artificial sequence
<220> FEATURE:
<223> OTHER INFORMATION: shRNA

<400> SEQUENCE: 20
tcttctaagc actgaagag                                              19

<210> SEQ ID NO 21
<211> LENGTH: 21
<212> TYPE: DNA
<213> ORGANISM: artificial sequence
<220> FEATURE:
<223> OTHER INFORMATION: ShRNA

<400> SEQUENCE: 21
ttactgaaca cgatcagcag g                                           21

<210> SEQ ID NO 22
<211> LENGTH: 19
<212> TYPE: DNA
<213> ORGANISM: artificial sequence
<220> FEATURE:
```

```
<223> OTHER INFORMATION: ShRNA

<400> SEQUENCE: 22
tactgaacac gatcagcag                                                    19

<210> SEQ ID NO 23
<211> LENGTH: 19
<212> TYPE: DNA
<213> ORGANISM: artificial sequence
<220> FEATURE:
<223> OTHER INFORMATION: ShRNA

<400> SEQUENCE: 23
ataaatatct gttcccaag                                                    19

<210> SEQ ID NO 24
<211> LENGTH: 19
<212> TYPE: DNA
<213> ORGANISM: artificial sequence
<220> FEATURE:
<223> OTHER INFORMATION: ShRNA

<400> SEQUENCE: 24
ttcttgtaaa taatgagcg                                                    19

<210> SEQ ID NO 25
<211> LENGTH: 19
<212> TYPE: DNA
<213> ORGANISM: artificial sequence
<220> FEATURE:
<223> OTHER INFORMATION: ShRNA

<400> SEQUENCE: 25
ttctcataaa tcttgttcg                                                    19

<210> SEQ ID NO 26
<211> LENGTH: 19
<212> TYPE: DNA
<213> ORGANISM: artificial sequence
<220> FEATURE:
<223> OTHER INFORMATION: ShRNA

<400> SEQUENCE: 26
ttccagtaga agtagtact                                                    19

<210> SEQ ID NO 27
<211> LENGTH: 21
<212> TYPE: DNA
<213> ORGANISM: artificial sequence
<220> FEATURE:
<223> OTHER INFORMATION: ShRNA

<400> SEQUENCE: 27
ttggatctgt aaagacgcca c                                                 21
```

COMPOSITIONS AND METHODS FOR INHIBITING HYPDXIA INDUCED DAMAGE

CROSS REFERENCE TO RELATED APPLICATIONS

This application claims priority to U.S. Provisional application No. 61/697,366, filed on Sep. 6, 2012, and U.S. Provisional application No. 61/779,256, filed Mar. 13, 2013, the disclosures of each of which are incorporated herein by reference.

FIELD

The present disclosure relates generally to hypoxia and more particularly to prophylaxis and/or therapy of hypoxia-associated conditions.

BACKGROUND

Hypoxia is a state of lower than normal tissue oxygen tension. Hypoxia and decreased supply of nutrients are the hallmarks of ischemia. Hypoxia and ischemia have been implicated in a host of human diseases, including cancer, heart disease, and neurological disorders. Additionally, organs and tissues which are obtained for transplantation frequently deteriorate due at least in part to hypoxia while being stored and transported for transplantation. Compositions and methods for treating hypoxia-associated diseases or conditions are needed. The present disclosure meets these needs.

SUMMARY OF THE DISCLOSURE

The present disclosure relates generally to compositions and methods for prophylaxis and/or therapy of disorders that are associated with hypoxia. In general, the method comprises administering to an individual, or to an organ or tissue, or to a cell culture, a composition comprising at least one agent that can inhibit the expression and/or function of at least one hypoxia related gene. The hypoxia related genes are genes known in the art as BCL2L14, BLOC1S2, C2ORF42, CPT1A, FBP1, GCNT3, RHOB, SCIN, TACR1 and TNFAIP6. These genes are referred to herein as "hypoxia related genes" or "HRGs."

cDNA sequences GenBank accession numbers for these HRGs are provided in Table 1 and in the sequence listing. The method involves use of any one or any combination of agents to suppress expression and/or function of the HRGs, and as a result, inhibit hypoxia-induced damage. In embodiments, at least two of the HRGs are inhibited by performing a method described herein. In embodiments, at least two gene inhibiting agents are used. In embodiments, at least two inhibiting agents targeted to the same HRGs are used.

The compositions comprise agents that can cause inhibition of the expression of the HRGs, or can inhibit the function of the proteins encoded by these genes. In embodiments, the agents are polynucleotide agents that can participate in RNAi-mediated degradation of the mRNAs encoded by the HRGs, or they are other compounds, such as small molecule compounds or specific binding partners, such as antibodies, which can interfere with the function of the proteins encoded by the HRGs. Polynucleotides can be administered in any suitable form and route, including but not necessarily limited to viral vectors which deliver shRNAs. In embodiments, a chemical (i.e., non-nucleic acid, non-protein) inhibitor is used. In an embodiment, the chemical inhibitor inhibits the function of TACR1. The inhibiting agents can be combined with one another to improve the capability to reduce hypoxia-induced damage.

In another aspect, kits comprising one or more HRG inhibiting agents. The kits can comprise printed material which can identify the HRG inhibiting agents and describe their use for inhibiting hypoxia-induced damage to an individual, and/or to an organ or tissue, and/or to a cell culture.

DETAILED DESCRIPTION

Figure 1:
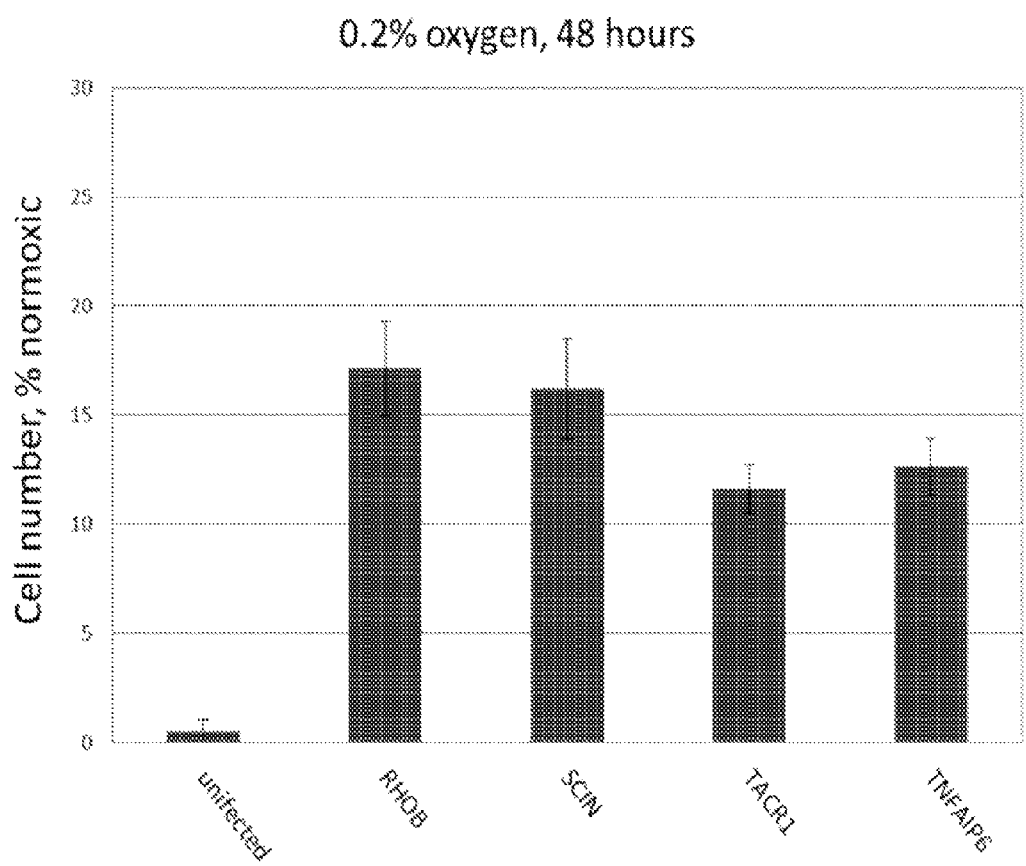
FIG. 1 provides a graphical summary of data obtained from testing of cells transduced by individual shRNAs, as per Protocol 2 as described in the Examples. The gene targets of individual shRNAs are indicated.
Figure 2:
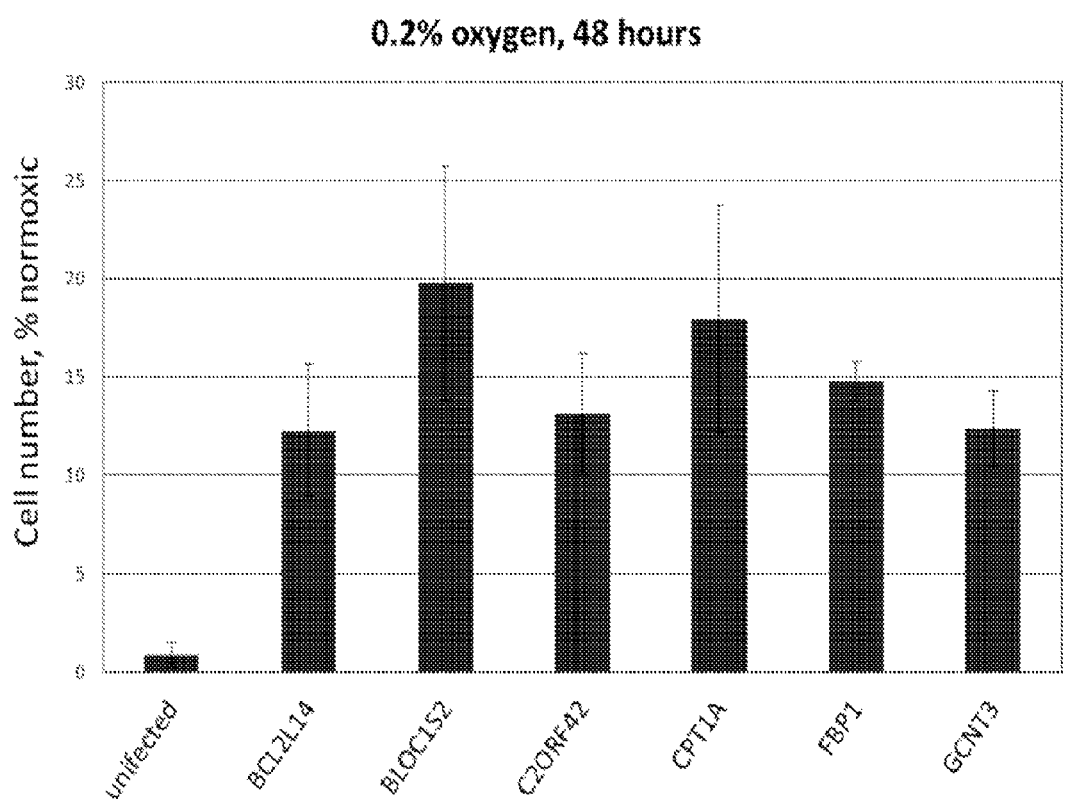
FIG. 2 provides a graphical summary of data obtained from testing of cells transduced by individual shRNAs, as per Protocol 2 as described in the Examples. The gene targets of individual shRNAs are indicated.
Figure 3:
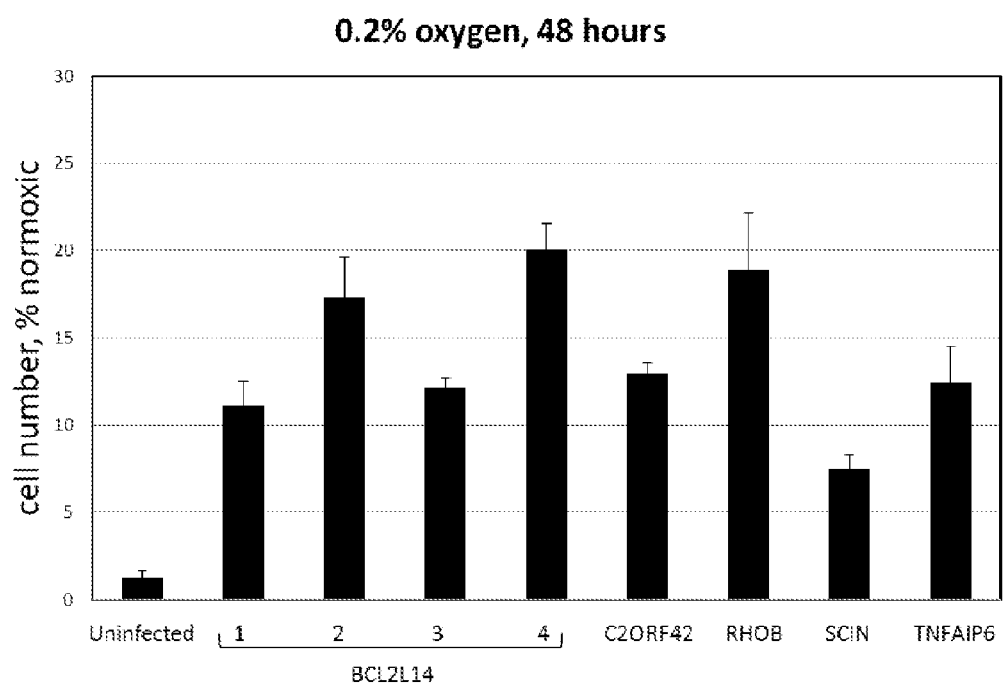
FIG. 3 provides a graphical summary of data obtained from testing of cells transduced by individual shRNAs, as per Protocol 2 as described in the Examples. The targets of individual shRNAs are indicated. Four distinct BCL2L14-specific shRNAs are were tested (bracketed in FIG. 3). They correspond, from left to right, to SEQ ID NO:11, 12, 13, 14.

The present disclosure provides compositions and methods for prophylaxis and/or therapy of hypoxia-associated conditions. The method generally comprises delivering to an individual, an organ, a tissue, or to a cellular composition comprising at least one agent that is capable of suppressing the expression and/or function of at least one of the following HRGs: BCL2L14, BLOC1S2, C2ORF42, CPT1A, FBP1, GCNT3, RHOB, SCIN, TACR1, TNFAIP6.

The accession numbers and sequence identifiers corresponding to the HRGs are as follows:

TABLE 1

| GENE NAME | GENEBANK ACCESSION NUMBER |
| --- | --- |
| BCL2L14 | NM_138722.1 (SEQ ID NO: 1) |
| BLOC1S2 | NM_173809.4 (SEQ ID NO: 2) |
| C2ORF42 | NM_017880.1 (SEQ ID NO: 3) |
| CPT1A | NM_001876.3 (SEQ ID NO: 4) |
| FBP1 | NM_000507.3 (SEQ ID NO: 5) |
| GCNT3 | NM_004751.2 (SEQ ID NO: 6) |
| RHOB | NM_004040.2 (SEQ ID NO: 7) |
| SCIN | NM_001112706.2 (SEQ ID NO: 8) |
| TACR1 | NM_001058.3 (SEQ ID NO: 9) |
| TNFAIP6 | NM_007115.3 (SEQ ID NO: 10) |

The nucleotide and amino acid sequences associated with each accession number provided here are incorporated herein as present in the GenBank database as of the filing date of this application. Each of the cDNA sequences associated with each of these genes is included with the sequence listing that is part of this disclosure. Those skilled in the art will be readily able to determine the polypeptide sequences encoded by the cDNA sequences from the cDNA sequences themselves, or from the amino acid sequence that are provided with the aforementioned GenBank database entries, if such a determination is necessary for any particular embodiment of the disclosure.

In certain aspects, the method is used for prophylaxis and/or therapy of undesirable consequences of hypoxia. Various aspects of the invention provide for treatment of an individual, an organ, a tissue or a cellular composition that is at risk for developing or has developed a disorder or other undesirable characteristic that is caused by and/or is positively correlated with the appearance hypoxia.

In producing the presently disclosed data we have discovered that functional suppression of one or more of these HRGs, either by inhibition of expression or by interference with the roll of the protein encoded by the HRG, can increase survival of cells under hypoxic conditions. In particular, in addition to using distinct proximal tubule cell lines to demonstrate this effect, we have demonstrated the validity of our approach using a clinically relevant animal model, namely using a mouse model of acute kidney ischemia. We have demonstrated that the protective/therapeutic effect can be achieved using two disparate approaches, namely, by using an RNAi-mediated approach, and by using chemical inhibition of the protein encoded by the HRGs. Further, we demonstrate that combined functional inhibition of at least two of the genes confers a protective effect that is greater than the effect of using either agent alone. Accordingly, we have demonstrated using multiple approaches that by inhibiting one or a combination of the genes described herein that generation of hypoxia-induced damage can be inhibited.

Any one or any combination or subcombination of the HRGs described herein can be suppressed to achieve prophylaxis and/or therapy of a condition associated with hypoxia. Thus, the method can comprise administering agents that can inhibit 1, 2, 3, 4, 5, 6, 7, 8, 9, or 10 of the HRGs disclosed herein. Additional HRGs not disclosed herein, or other anti-hypoxia agents can also be administered. In addition to inhibition of any one or any combination of the HRGs, any number of agents can be used, such that more than one agent targeted to any single HRG can be employed. In embodiments, at least one of the HRGs is inhibited by using at least two agents targeted to it. In certain embodiments, the method involves targeting at least one HRG with at least two shRNAs.

In one embodiment, functional suppression of TACR1 is effected by the invention. In one embodiment, a plurality of HRGs which is suppressed by the performing the invention includes inhibition of TACR1, RhoB, or a combination of TACR1 and RhoB.

Agents that are capable of functional repression of an HRG are those that interfere with expression of the HRG and/or function of an HRG protein. Interfering with expression includes but is not necessarily limited to methods involving use of nucleic acids as inhibiting agents, such as by hybridization of a polynucleotide to DNA and/or RNA encoding an HRG. In alternative embodiments, the method involves the use of chemical inhibitors (i.e., chemotherapeutic agents or other small-molecule based approaches).

In one embodiment, the invention includes administering to an individual or a tissue or a cell culture an shRNA as described herein, or a chemotherapeutic agent, or a combination thereof. In one embodiment, the chemotherapeutic agent is (2S,3S)-3-{[3,5-bis(trifluoromethyl)benzyl]oxy}-2-phenylpiperidine (also known as L-733,060), which is an inhibitor of TACR1 gene product. This compound is commercially available. It is a member of a class of compounds which have been approved by the US Food and Drug Administration for therapy of depression, and for nausea but has never been proposed for use of prophylaxis and/or therapy of hypoxia.

Agents that hybridize to DNA and/or RNA encoding an HRG can facilitate suppression by impeding HRG mRNA transcription and/or translation, and/or by causing degradation of HRG mRNA. For example, when the agent is a polynucleotide, the agent may be an RNA polynucleotide, a DNA polynucleotide, or a DNA/RNA hybrid. The polynucleotide may comprise a ribozyme, such as a hammerhead ribozyme, or it may comprise a DNAzyme, a hairpin ribozyme, an antisense RNA, or an siRNA, or any modified or unmodified polynucleotide capable of inhibiting HRG by a process that includes hybridizing to HRG mRNA or DNA. Methods for designing ribozymes, antisense RNA, siRNA, and DNAzymes are well known in the art. It will be recognized that any such agent will act at least in part via hybridization to RNA or DNA sequences of an HRG. Thus, the polynucleotide agents of the present invention will have sufficient length and complementarity with RNA or DNA of an HRG so as to hybridize to the RNA or DNA under physiological conditions. In general, at least approximately 10 continuous nucleotides of the polynucleotide agent should be complementary or identical to the HRG DNA or RNA.

The polynucleotide agent may include modified nucleotides and/or modified nucleotide linkages so as to increase the stability of the polynucleotide. Suitable modifications and methods for making them are well known in the art. Some examples of modified polynucleotide agents for use in the present invention include but are not limited to polynucleotides which comprise modified ribonucleotides or deoxyribonucleotides. For example, modified ribonucleotides may comprise substitutions of the 2' position of the ribose moiety with an —O— lower alkyl group containing 1-6 saturated or unsaturated carbon atoms, or with an —O-aryl group having 2-6 carbon atoms, wherein such alkyl or aryl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group. The nucleotides may be linked by phosphodiester linkages or by a synthetic linkage, i.e., a linkage other than a phosphodiester linkage. Examples of inter-nucleoside linkages in the polynucleotide agents that can be used in the invention include but are not limited to phosphodiester, alkylphosphonate, phosphorothioate, phosphorodithioate, phosphate ester, alkylphosphonothioate, phosphoramidate, carbamate, carbonate, morpholino, phosphate trister, acetamidate, carboxymethyl ester, or combinations thereof.

In one embodiment, the agent is an siRNA for use in RNA interference (RNAi) mediated silencing or downregulation of HRG mRNA. RNAi agents are commonly expressed in cells as short hairpin RNAs (shRNA). shRNA is an RNA molecule that contains a sense strand, antisense strand, and a short loop sequence between the sense and antisense fragments. shRNA is exported into the cytoplasm where it is processed by dicer into short interfering RNA (siRNA). siRNA are 21-23 nucleotide double-stranded RNA molecules that are recognized by the RNA-induced silencing complex (RISC). Once incorporated into RISC, siRNA facilitate cleavage and degradation of targeted mRNA. Thus, for use in RNAi mediated silencing or downregulation of HRG expression, the polynucleotide agent can be either an siRNA or an shRNA. Representative but non-limiting shRNAs for use in various aspects of the instant disclosure are provided in Table 2.

shRNA of the invention can be expressed from any suitable vector such as a recombinant viral vector either as two separate, complementary RNA molecules, or as a single RNA molecule with two complementary regions. In this regard, any viral vector capable of accepting the coding sequences for the shRNA molecule(s) to be expressed can be used. Examples of suitable vectors include but are not limited to vectors derived from adenovirus, adeno-associated virus, retroviruses (e.g, lentiviruses, Rhabdoviruses, murine leukemia virus), herpes virus, and the like. A preferred virus is a lentivirus. The tropism of the viral vectors can also be modified by pseudotyping the vectors with envelope proteins or other surface antigens from other viruses. As an alternative to expression of shRNA in cells from a recombinant vector, chemically stabilized shRNA or siRNAs may also be used administered as the agent in the method of the invention. Vectors for expressing shRNA which in turn produces siRNA once introduced into a cell are commercially available. Further, shRNAs which facilitate produce of siRNA targeted to virtually every known human gene are also known and are commercially available. In embodiments specific shRNAs are those which comprise polynucleotide sequences presented in Table 2, wherein those sequences are targeted to the genes as indicated. In particular, Table 2 provides the sequence of segments of shRNAs that target the HRGs of the present disclosure. The rightmost column shows the geometric mean (2-6 independent experiments) of fold increase in the number of viable cells remaining after hypoxia treatment of appropriately modified HK-2 cells, as compared to the control HK-2 cells, as further detailed in the Examples (Protocol 2) of this disclosure. "RPCI" under source designates the "shRNA Resource of Roswell Park Cancer Institute" which distributes shRNAs from commercial vendors. The catalog # column signifies a reference under which each of the shRNAs are made available to the public. The SEQ ID # column refers to the sequence listing that forms a part of this disclosure. The polynucleotide sequences provided in Table 2 are cDNA sequences that recognize the target gene mRNA via shRNA. It will be recognized by those skilled in the art that the shRNAs used in the Examples presented herein have the identical sequences as listed in Table 2, except for substitution of each thymine with uracil. It will be also recognize that each of the shRNAs as used in practice has additional sequences that are typical of shRNA constructs, but that the sequences listed in Table 2 are the ones that are antisense to the mRNA of the indicated HRGs.

TABLE 2

| target gene | antisense sequence | SEQ ID # | source | catalog # | geometric mean of fold increase in cell number |
|---|---|---|---|---|---|
| BCL2L14 | TCTTGCCAAGGTTTATGGC | 11 | RPCI | V2LHS 194199 | 8 |
|  | ATCTCTTTGGACTTGAAGC | 12 | RPCI | V2LHS 203030 | 9 |
|  | TGATGTCTGGTGTAGTAGG | 13 | RPCI | V2LHS 238885 | 10 |
|  | ATCTCCTGAATATTTCAGCAG | 14 | Cellecta | N.A. | 13 |
| BLOC1S2 | ATGACATTGATCTGATCCA | 15 | RPCI | V2LHS 179388 | 23 |
| C2ORF42 | TCTTCAACAGAATCCACTT | 16 | RPCI | V2LHS 174286 | 6 |
|  | AAACGCTAAAGATGAGTCC | 17 | RPCI | V2LHS 223529 | 7 |
| CPT1A | ATTGGTTTGATTTCCTCCC | 18 | RPCI | V2LHS 150873 | 18 |
| FBP1 | AACATGTTCATAACCAGGTCG | 19 | Open Biosystems | TRCN0000050034 | 26 |
| GCNT3 | TCTTCTAAGCACTGAAGAG | 20 | RPCI | V2LHS 36116 | 11 |
| RHOB | TTACTGAACACGATCAGCAGG | 21 | Open Biosystems | TRCN0000047849 | 22 |
|  | TACTGAACACGATCAGCAG | 22 | RPCI | V2LHS 262482 | 9 |
| SCIN | ATAAATATCTGTTCCCAAG | 23 | RPCI | V2LHS 159985 | 15 |
|  | TTCTTGTAAATAATGAGCG | 24 | RPCI | V2LHS 159984 | 5 |
| TACR1 | TTCTCATAAATCTTGTTCG | 25 | RPCI | V2LHS 94027 | 15 |
| TNFAIP6 | TTCCAGTAGAAGTAGTACT | 26 | RPCI | V2LHS 206501 | 12 |
|  | TTGGATCTGTAAAGACGCCAC | 27 | Cellecta | N.A. | 5 |

In another embodiment, the agent may be an antibody that recognizes an HRG encoded protein (an "HRG protein").

The antibodies used in the invention will accordingly bind to an HRG protein such that the binding of the antibody interferes with the activity of the HRG protein.

Antibodies that recognize HRG protein for use in the invention can be polyclonal or monoclonal. It is preferable that the antibodies are monoclonal. Methods for making polyclonal and monoclonal antibodies are well known in the art. It is expected that antigen-binding fragments of antibodies may be used in the method of the invention. Examples of suitable antibody fragments include Fab, Fab', F(ab')$_2$, and Fv fragments. Various techniques have been developed for the production of antibody fragments and are well known in the art. It is also expected that the antibodies or antigen binding fragments thereof may be humanized.

In alternative embodiments, the agent that suppresses HRGs described herein is a small-molecule HRG inhibitor. One such inhibitor is (2S,3S)-3-{[3,5-bis(trifluoromethyl) benzyl]oxy}-2-phenylpiperidine (also known as L-733,060), which is an inhibitor of TACR1 gene product.

Compositions comprising an agent that can suppress one or more HRGs for use in therapeutic purposes may be prepared by mixing with any suitable pharmaceutically acceptable carriers, excipients and/or stabilizers. Some examples of compositions suitable for mixing with the agent can be found in: Remington: The Science and Practice of Pharmacy (2005) 21st Edition, Philadelphia, Pa. Lippincott Williams & Wilkins. Combinations of agents can be used so that more than one HRG can be suppressed are included within the scope of the invention.

If the agent is a polynucleotide, it can be administered to the individual as a naked polynucleotide, in combination with a delivery reagent, or as a recombinant plasmid or viral vector which either comprises or expresses the polynucleotide agent. Suitable delivery reagents for administration include the Minis Transit TKO lipophilic reagent; lipofectin; lipofectamine; cellfectin; or polycations (e.g., polylysine), or liposomes.

In general, a formulation for therapeutic use according to the method of the invention comprises an amount of agent effective to suppress expression of one or more HRGs. Those skilled in the art will recognize how to formulate dosing regimens for the agents of the invention, taking into account such factors as the molecular makeup of the agent, the size and age of the individual to be treated, and the type and location of the hypoxia that is to be suppressed. The formulations can be administered prior to, concurrently with, or subsequent to any other anti-hypoxia agent or technique used to mitigate hypoxia and/or damage associated therewith.

Compositions comprising one or more agents for suppression of one or more HRGs can be administered to an individual using any available method and route suitable for drug delivery, including parenteral, subcutaneous, intraperitoneal, intrapulmonary, and intranasal. Parenteral infusions include intramuscular, intravenous, intraarterial, intraperitoneal, and subcutaneous administration.

In one embodiment, the invention comprises a method for prophylaxis and/or therapy of hypoxia in an individual or in an organ or tissue removed from an individual. In the case of an individual thehypoxia can be chronic or acute. The method comprises delivering to the individual or to the organ or to the tissue a composition comprising one or more agents which are capable of inhibiting one or more of the genes disclosed herein such that cellular damage from hypoxia in the individual, organ or tissue is inhibited and/or reduced subsequent to delivery of the composition. A reduction in or inhibition of cytotoxicity of hypoxia can be evidenced in a variety of ways known to those skilled in the art, such as by a reduction in cell death or markers thereof in cells, tissues or organs exposed to hypoxic conditions and to which a composition of the invention has been delivered.

In one embodiment, the invention comprises a method for reducing damage from hypoxia in a cellular composition. Thus, by contacting cells in vitro with a hypoxia-reducing agent the cells can be made resistant to hypoxic conditions. The in vitro cells can be comprise of any cells, including but not necessarily limited to immortalized cells used for research purposes, or stem cells, or cells that are pluripotent or multipotent, such as hematopoietic stem cells.

Any change in gene expression and/or a change in hypoxia facilitated by the invention can be determined using well known techniques. Any such changes can be detected and/or quantified by comparison to a reference, such as a positive or negative control, or a standardized reference value. In embodiments, the reference is the level of expression and/or function of an HRG in a cell that is not exposed to hypoxia.

Conditions involving hypoxia include but are not limited to occlusive arterial disease, angina pectoris, intestinal infarctions, pulmonary infarctions, cerebral ischemia, acute kidney injury, chronic kidney disease and myocardial infarction. Tissue damage caused by or related to hypoxia can occur due to diseases such as atherosclerosis, diabetes, stroke, and pulmonary disorders such as pulmonary embolism and the like. The invention is therefore expected to be suitable for prophylaxis and/or therapy of a wide variety of hypoxia-related conditions which include but are not necessarily limited to cardiovascular disease, heart disease, stroke, macular degeneration, diabetic retinopathy, arthritis, inflammation, tissue fibrosis, gastrointestinal disease, neurodegenerative disease, respiratory distress syndrome, bronchopulmonary displasia, pulmonary hypertension, hypoxic pulmonary hypertension, severe pulmonary hypertension, COPD, diabetic retinopathy, diabetes, corneal neovascularization, pathogenic blood vessel growth, musculoskeletal disorders, ischemic-reperfusion injury, myocardial hypoxia, cardiac hypertrophy, various types of cancers and renal disease. In this regard, kidney tubular epithelial cells are very sensitive to hypoxia. The death of these cells may lead to acute kidney failure, or to more delayed health problems. The presence of damaged cells also contributes to inflammation during reperfusion of a previously ischemic kidney, which can result in lost epithelial cells being replaced by connective tissue (kidney fibrosis). Both inflammation and fibrosis may lead to eventual organ failure. Furthermore, the death of epithelial cells in a severed organ is one of the primary causes of failure of kidney transplantation. To reduce cell death, the organ to be transplanted is kept refrigerated; however, this causes various adverse effects due to cold shock, and cold ischemia time still remains a strong predictor of short and long-term graft survival. Furthermore, hypoxia accompanied by reduced availability of glucose is known to be toxic to a wide variety of cell types and tissues, and the fundamental biochemical processes allegedly affected by these conditions are likely to be relevant to ischemic response of multiple organs. Thus, in one embodiment, the method is used to inhibit hypoxia in an organ that is removed from an individual for transplantation. In various embodiments, the organs are selected from a heart, a lung, a pancreas, a liver, and a kidney. In one embodiment, the organ is a kidney. The method generally comprises delivering to the organ a therapeutically effective amount of a composition that suppresses one or more of the genes disclosed herein. The composition can be administered to the organ ex vivo using any of a number of techniques. In non-limiting examples, the composition can be injected directly into the organ, or it can be delivered to the organ during any conventional perfusion technique by adding a pharmaceutical preparation comprising one or more HRG suppression agents to a perfusion solution. For example, the preparation could be added to one of the solutions sold under the trade name Viaspan (also referred to as "UW" solution), or Celsior, or a solution known as the Kyoto solution, or Bretschneider's HTK solution. The compositions could also be used by delivering to the organ during simple cold storage when flushed with a cold preservation fluid. The composition could be used during continuous hypothermic perfusion, such as during machine perfusion.

In an embodiment, the present disclosure includes articles of manufacture for use of HRG inhibition in the prophylaxis and/or therapy of damage caused by hypoxia. The products comprise one or more HRG inhibiting agents, such as one or more delivery vectors encoding shRNA(s) described herein, and also packaging and/or printed material. In one embodiment, the instant disclosure includes a closed or sealed package that contains a HRG inhibiting agents in a pharmaceutical preparation. In certain embodiments, the package can comprise one or more closed or sealed vials, bottles, blister (bubble) packs, or any other suitable packaging for the sale, or distribution, or use of the HRG-inhibiting pharmaceutical agents. In addition to the HRG inhibiting agent compositions, the package may contain printed information. The printed information can be provided on a label, or on a paper insert, or printed on the packaging material itself. The printed information can include information that identifies the HRG inhibiting agent(s) in the package, the amounts and types of other active and/or inactive ingredients, and instructions for administering the composition. The printed material can include an indication that the HRG inhibiting agent(s) are for the prophylaxis and/or therapy of hypoxia related conditions, such as those that can affect an individual, an ex vivo organ or tissue, or a cell culture. The product can be provided as a kit comprising a therapeutically effective amount of a HRG inhibiting agent(s).

The following specific examples are provided to illustrate the invention, but are not intended to be limiting in any way.

EXAMPLE 1

This Example provides a description of the identification of genes whose products could be targeted for us in prophylaxis and/or therapy of hypoxia. In order to identify the genes whose products could be targeted for inhibition in order to improve cell survival under hypoxic conditions, we undertook a genetic screen of a lentivirally-delivered shRNA library (Human Decipher Modules 1, 2 and 3 from Cellecta, Inc.) in a kidney epithelial cell lines referred to in the art as HK-2 cells. The library contains close to 80000 different shRNAs, which correspond to close to 16000 human genes. Each of the shRNAs is cloned alongside a unique bar-code, so that the relative frequency of individual shRNA constructs in a pool of cells could be estimated upon PCR-amplification and sequencing of the pool of the tags. Following the procedures outlined below, candidate shRNAs and the respective genes were identified and further confirmed in individual testing using alternative shRNAs or chemical inhibitors. We also tested a chemical inhibitor alone and in combination with the shRNA agents. Specific experimental protocols were as follows.

Protocol 1: Large-scale screen of shRNA library Day 0: $6 \times 10^6$ HK-2 cells were seeded on each of nine 150 mm dishes. Day 1: Cells were transduced with a library containing ~$8 \times 10^4$ shRNAs corresponding to ~$1.6 \times 10^4$ genes with the intention of achieving an MOI of 0.3-0.4. Day 2: The media containing the virus was exchanged for fresh keratinocyte media. Day 3: The cells were divided into three groups or "replicas" (3 dishes per group). Cells from each replica were pooled together, and then seeded into six dishes, each containing around $6 \times 10^6$ cells. Day 4: Keratinocyte medium was removed from the dishes, and fresh DMEM containing low glucose was added. Three of the dishes from each group were transported to a chamber containing 0.2% oxygen for 48 hours, while the others remained at normoxia for the same period of time. Day 6: Cells in the hypoxia chamber were returned to normal growth conditions for recovery and expansion and the untreated cells were selected with antibiotic to enrich for those containing shRNAs. Day 9: Cells that were exposed to 48-hour hypoxia treatment were selected with antibiotic to enrich for those containing shRNAs. Following sufficient expansion the cells were frozen and submitted for sequencing of the recovered bar-codes. Sequencing service and bar-code enumeration was provided by Cellecta, Inc. The incidence of individual shRNAs in cells from the same replica grown in normoxic vs. hypoxic conditions was compared. A sample of genes for individual testing was taken from a list based on consistent (twice or trice out of 3 replicas) enrichment of at least 2 distinct shRNAs, which correspond to the same gene.

Protocol 2: Individual shRNA screening.

Cell Preparation: Lentiviral vectors containing various shRNAs of interest were obtained from commercial sources, and packaged in 293T cells. HK-2 cells were then transduced with these expression constructs and selected for the presence of a vector-encoded antibiotic resistance marker.

Hypoxia Protocol: Day 0: HK-2 cells containing individual shRNAs were seeded in triplicate on two 96-well plates, $3 \times 10^4$ cells/well. Negative controls included uninfected cells or cells infected with a corresponding empty vector. Day 1: Keratinocyte medium was removed from the plates and fresh DMEM containing low glucose was added. One of the plates was then transported to a chamber that contained 0.2% oxygen for 48 hours, while the other remained at normoxia for the same period of time. Day 3: The cells were rescued from hypoxia and the plates were immediate fixed and stained with methylene blue to assess survival. Results were then graphed as the percent of stain of the corresponding cells incubated in normoxic conditions minus the background (non-specific dye absorption by empty wells).

Figure 4:
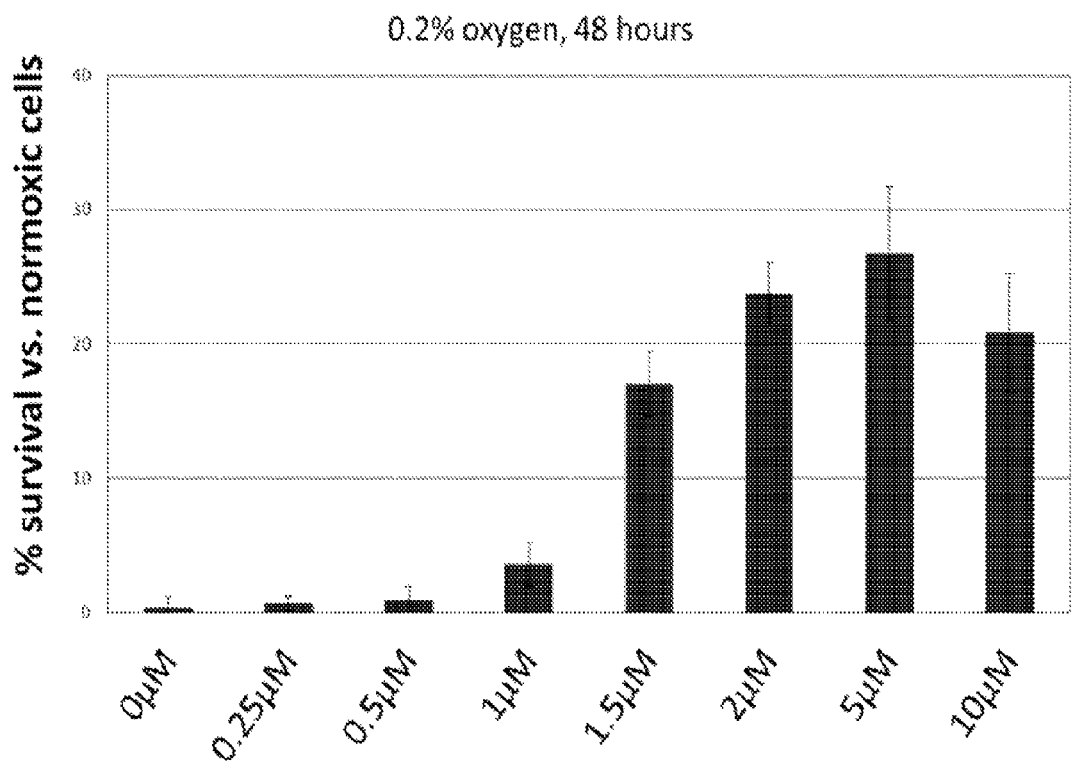
FIG. 4 provides a graphical summary of data obtained by testing of cells treated by a chemical inhibitor of TACR1 gene product, as per Protocol 3 as described in the Examples.

Protocol 3: Testing TACR1 inhibitor. Day 0: HK-2 cells were seeded on two 96-well plates, $3 \times 10^4$ cells/well. Day 1: Keratinocyte medium was removed from the plates and fresh DMEM containing low glucose and the indicated concentration of the TACR1 inhibitor (L-733,060) was added. Concentrations investigated ranged from 0-10 μM, and each was examined in quadruplicate fashion. The two plates were incubated in the presence of the inhibitor at normal growth conditions for 1 hour, at which time one of the plates was transported to a chamber that contained 0.2% oxygen for 48 hours, while the other remained at normoxia for the same period of time. Day 3: The cells were rescued from hypoxia and the plates were immediate fixed and stained with methylene blue to assess survival. Results were then graphed as the percent of stain of the corresponding cells incubated in normoxic conditions minus the background (non-specific dye absorption by empty wells). FIG. 4: testing of cells treated by a chemical inhibitor of TACR1 gene product, as per Protocol 3.

Figure 5:
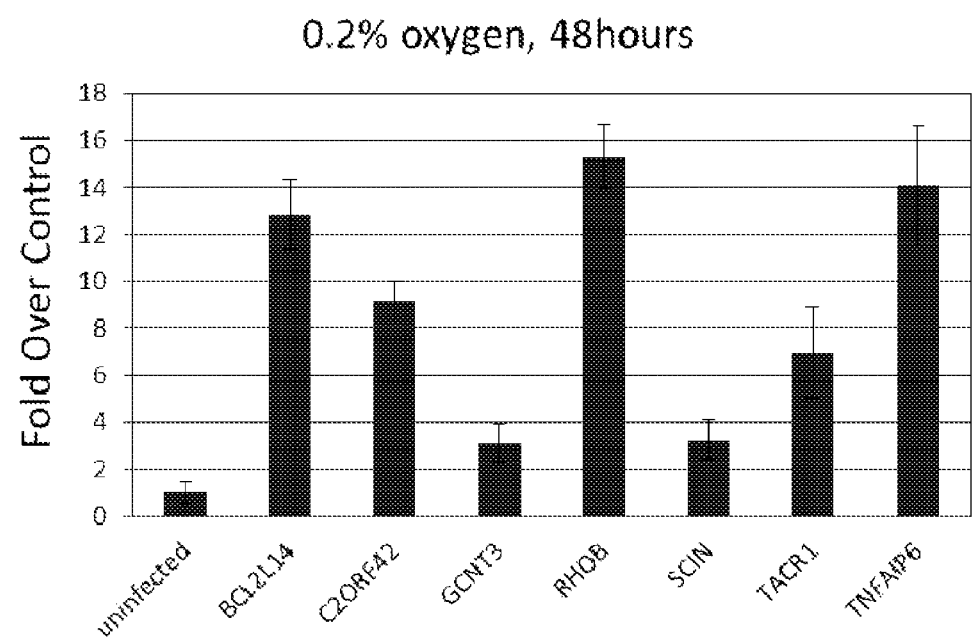
FIGS. 5 and 6 provide graphical summary of data obtained from testing individual shRNAs in hRPTEC cells (a clone of an HK-2-like cell line, which distinctly lacks Y-chromosome), as per Protocol 4 described in the Examples. The data is shown as fold-increase in the number of surviving cells over the uninfected cultures.
Figure 6:
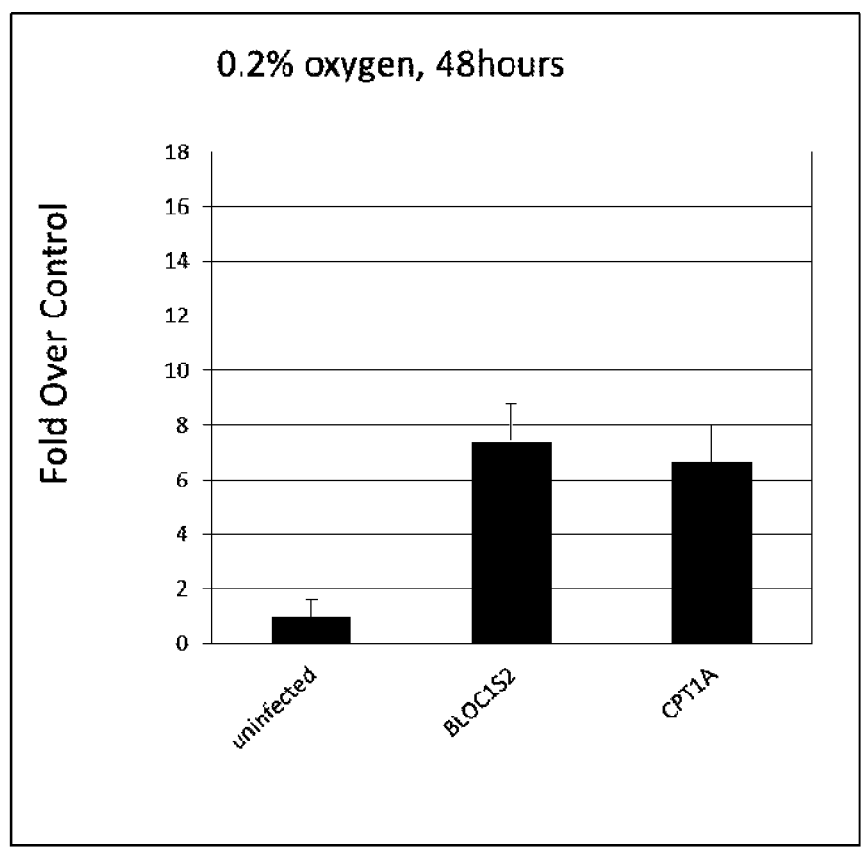

Protocol 4: Individual shRNA testing in hRPTEC cells. The following protocol was used to obtain data presented in FIGS. 5 and 6.

Cell Preparation: Lentiviral vectors containing various shRNAs of interest were obtained from commercial sources, and packaged in 293T cells. hRPTEC cells (a clone of HK-2-like cells, which lacks Y-chromosome) were then transduced with these expression constructs and selected for the presence of a vector-encoded antibiotic resistance marker.

Hypoxia Treatment: Day 0: hRPTECs containing individual shRNAs were seeded in triplicate on two 96-well plates, $2 \times 10^4$ cells/well. Negative controls included uninfected cells or cells infected with a corresponding empty vector. Day 1: Keratinocyte medium was removed from the plates and fresh DMEM containing low glucose was added. One of the plates was then transported to a chamber that contained 0.2% oxygen for 48 hours, while the other remained at normoxia for the same period of time. Day 3: The cells were rescued from hypoxia and the plates were immediate fixed and stained with methylene blue to assess survival. The percent of stain of the corresponding cells incubated in normoxic conditions minus the background (non-specific dye absorption by empty wells) was calculated as a measure of cell resistance to the hypoxia. The results were plotted as a fold increase in resistance over uninfected cells. The cultures transduced with the specified shRNAs showed a significant increase in remaining cells numbers, as is demonstrated in FIGS. 5 and 6.

Figure 7:
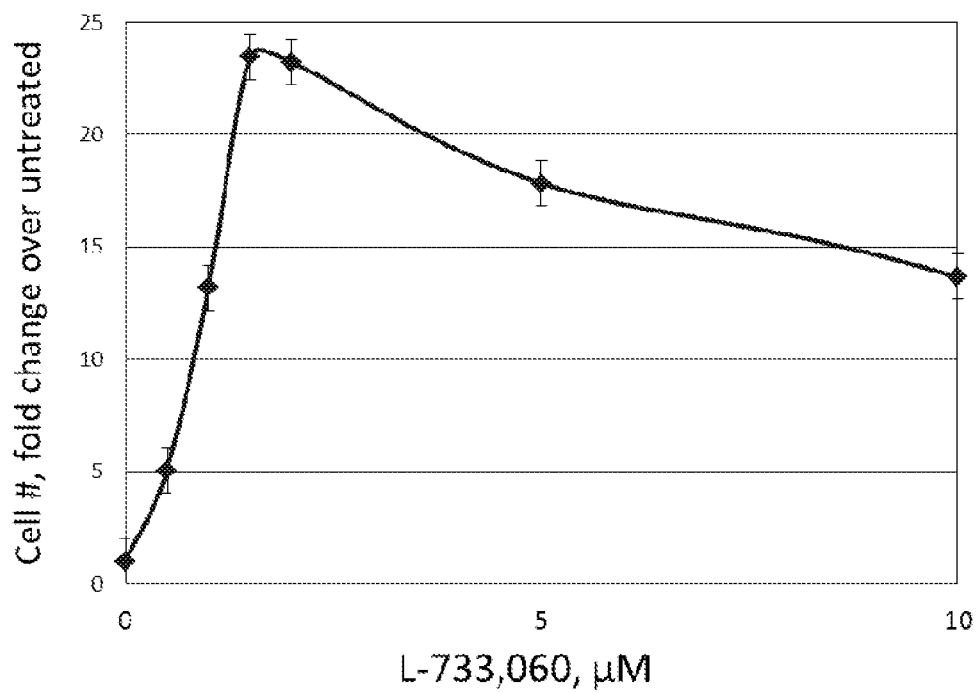
FIG. 7 provides a graphical summary of data which demonstrates that the protective effect of chemical inhibition of the identified genes is not limited to any single cell lines since chemical inhibition of TACR1 significantly increased survival of the different cells types.

The data presented in FIG. 7 demonstrate that the protective effect of chemical inhibition of the identified genes significantly increases survival of the hRPTEC cells. In this regard, we tested the effect of TACR1 protein inhibitor L-733,060 on these cells. The following protocol was used: Day 0: hRPTEC were seeded on two 96-well plates, $2 \times 10^4$ cells/well. Day 1: Keratinocyte medium was removed from the plates and fresh DMEM containing low glucose and the indicated concentration of the TACR1 inhibitor (L-733,060) was added. Each concentration was examined in quadruplicate fashion. The two plates were incubated in the presence of the inhibitor at normal growth conditions for 1 hour, at which time one of the plates was transported to a chamber that contained 0.2% oxygen for 48 hours, while the other remained at normoxia for the same period of time. Day 3: The cells were rescued from hypoxia and the plates were immediate fixed and stained with methylene blue to assess survival. The percent of stain of the corresponding cells incubated in normoxic conditions minus the background (non-specific dye absorption by empty wells) was calculated as a measure of cell resistance to the hypoxia. The results were plotted as a fold increase in resistance over that of cells not treated with L-733,060.

Figure 8:
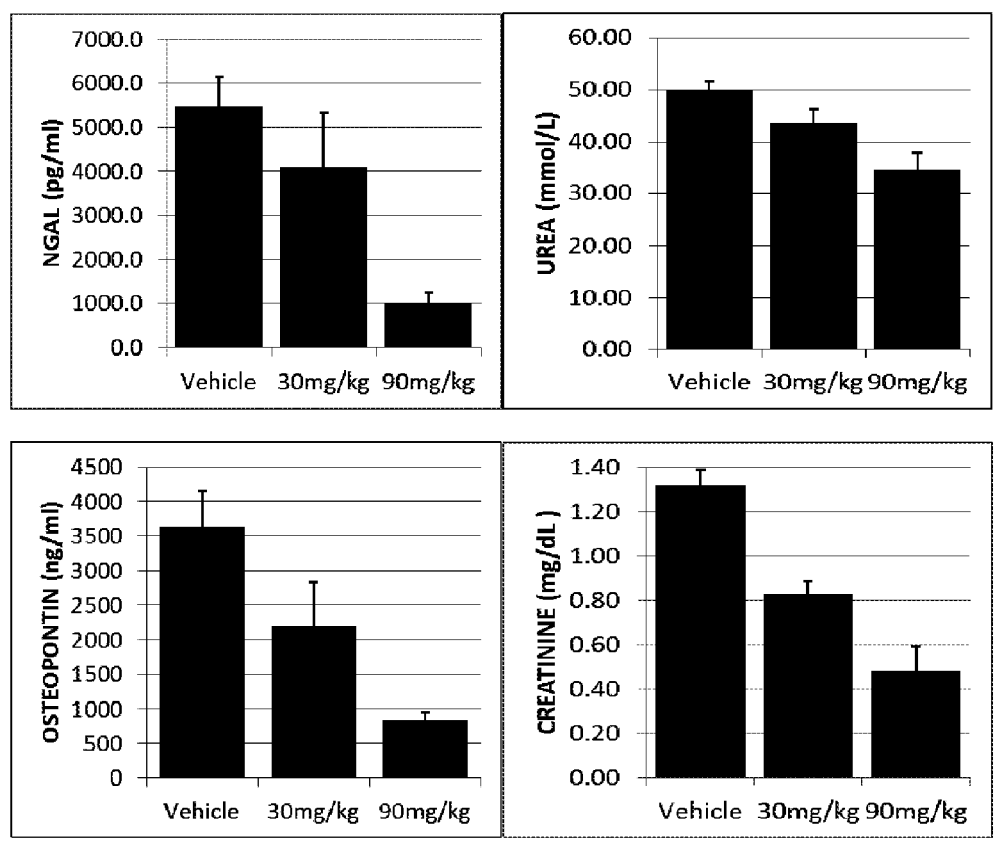
FIG. 8 provides a graphical summary of data which demonstrates that administration of a chemical inhibitor of an identified gene reduces the damage to kidneys in a mouse model of acute renal ischemia.

The data presented in FIG. 8 demonstrate that administration of a chemical inhibitor of TACR1 reduces the damage to kidneys in a mouse model of acute renal ischemia. In particular, the protective effects of chemically inhibiting TACR1 were examined in a mouse model of acute renal ischemia using the following protocol: i. 30 minutes before the surgery, mice received an i.p. injection of a TACR1 inhibitor (L-733,060) at either 30 mg/kg or 90 mg/kg, or of the respective vehicle (saline). ii. Under general anesthesia with Ketamin/Rompun, the mice were subjected to 25 min of ischemic of both kidneys. Each of the 2 kidneys was exposed through a flank incision. The kidney pedicle was clamped with atraumatic clamps for 25 min. iii. Mice were kept in an incubator at constant temperature 36 C during the 25 min of ischemia. After 25 min of ischemia, clamps were removed and wounds were closed. iv. 24 hrs after reperfusion blood samples were taken and mice were sacrificed. v. The levels of biochemical markers of kidney damage were measured in the plasma of the collected blood. Specifically, creatinine, neutrophil gelatinase-associated lipocalin (NGAL), osteopontin and urea (blood urea nitrogen) were measured. As indicated in FIG. 8, L-733,060 treatment decreases the appearance of signs of kidney damage.

Figure 9:
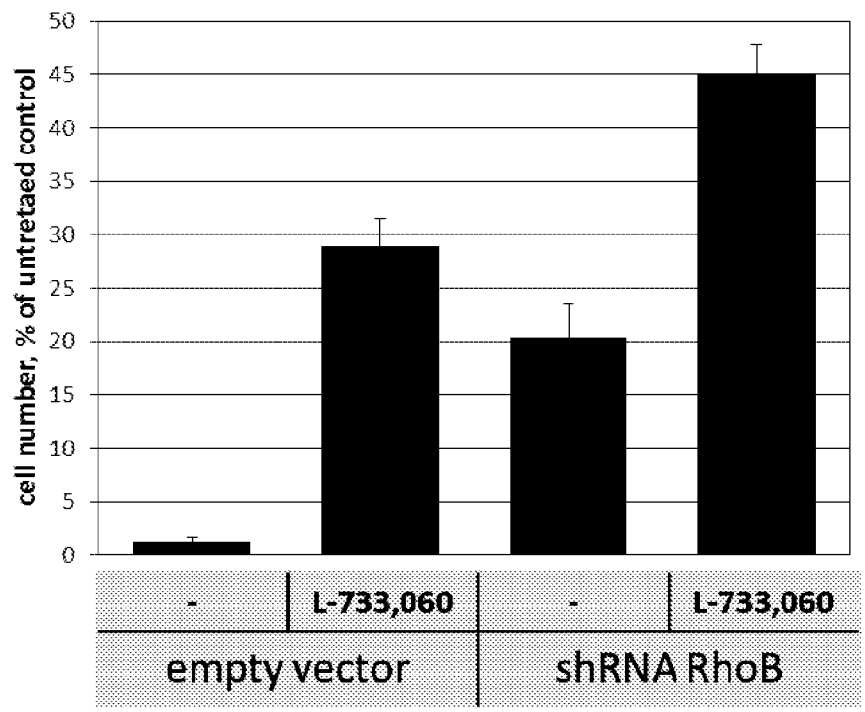
FIG. 9 provides a graphical summary of data which demonstrates that combined inhibition of RhoB and TACR1 using the indicated reagents provides better protection that either one alone.

We also demonstrate that combined inhibition of more than one of the identified genes increases the protective effect, as shown in FIG. 9. To obtain the data presented in FIG. 9, HK-2 cells were trasnduced with either a construct expressing an shRNA to RhoB (cell line "HK2-RhoB") or the corresponding empty vector (cell line "HK2-vector"). The survival of cells in hypoxic condition with or without addition of TACR1 inhibitor was evaluated using the following protocol: Day 0: HK-2 cells were seeded on two 96-well plates, $3 \times 10^4$ cells/well. Day 1: Keratinocyte medium was removed from the plates and fresh DMEM containing low glucose. TACR1 inhibitor (L-733,060; 5 μM) was added to half of the wells of either HK2-RhoB or HK2-vector. One hour later one of the plates was transported to a chamber that contained 0.2% oxygen for 48 hours, while the other remained at normoxia for the same period of time. Day 3: The cells were rescued from hypoxia and the plates were immediate fixed and stained with methylene blue to assess survival. Results were then graphed as the percent of stain of the corresponding cells incubated in normoxic conditions minus the background (non-specific dye absorption by empty wells). The results in FIG. 9 show that combined inhibition of RhoB and TACR1 using the indicated reagents provides better protection that inhibition of either one alone.

Figure 11:
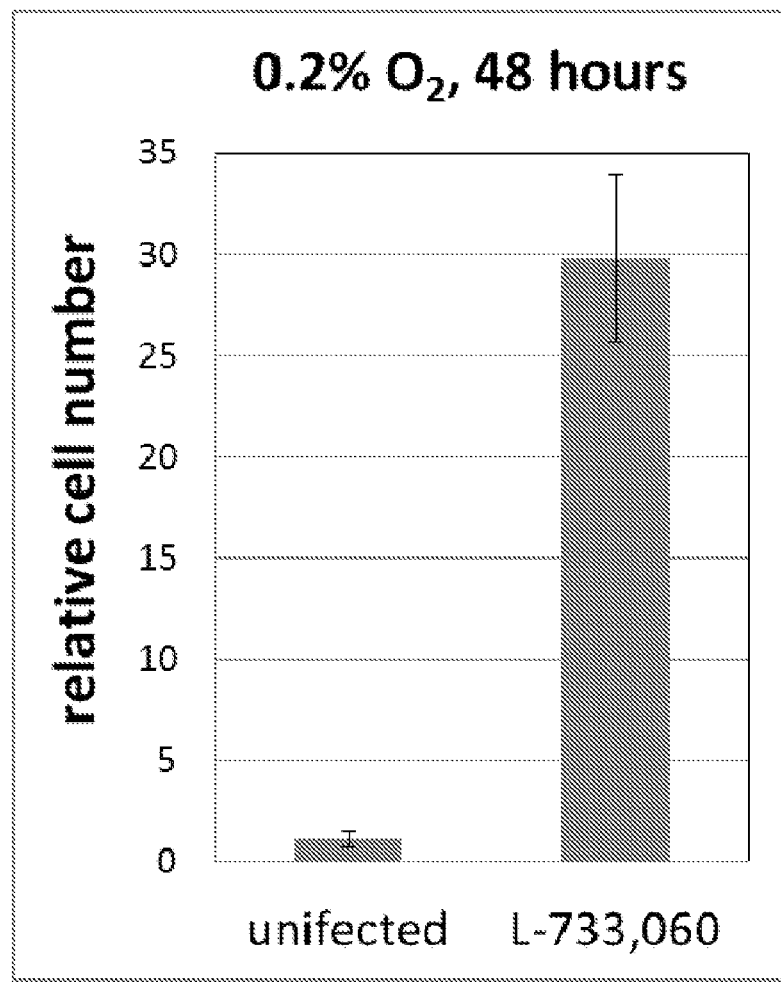
FIG. 11 provides a graphical summary of data which demonstrates that TACR1 inhibitor is strongly protective against the effects of hypoxia on HKC8 cells.

Data presented in FIGS. 11 and 12 were obtained using HKC8 cells which are a relevant model of kidney proximal tubular epithelium. To obtain these data, we tested the protective effects of select shRNAs in HKC8 cells using the following protocol.

Cell Preparation: Lentiviral vectors containing various shRNAs of interest were obtained from commercial sources, and packaged in 293T cells. HKC8 (non-cancerous immortalized proximal tubular epithelial kidney cells) were then transduced with these expression constructs and selected for the presence of a vector-encoded antibiotic resistance marker.

Figure 10:
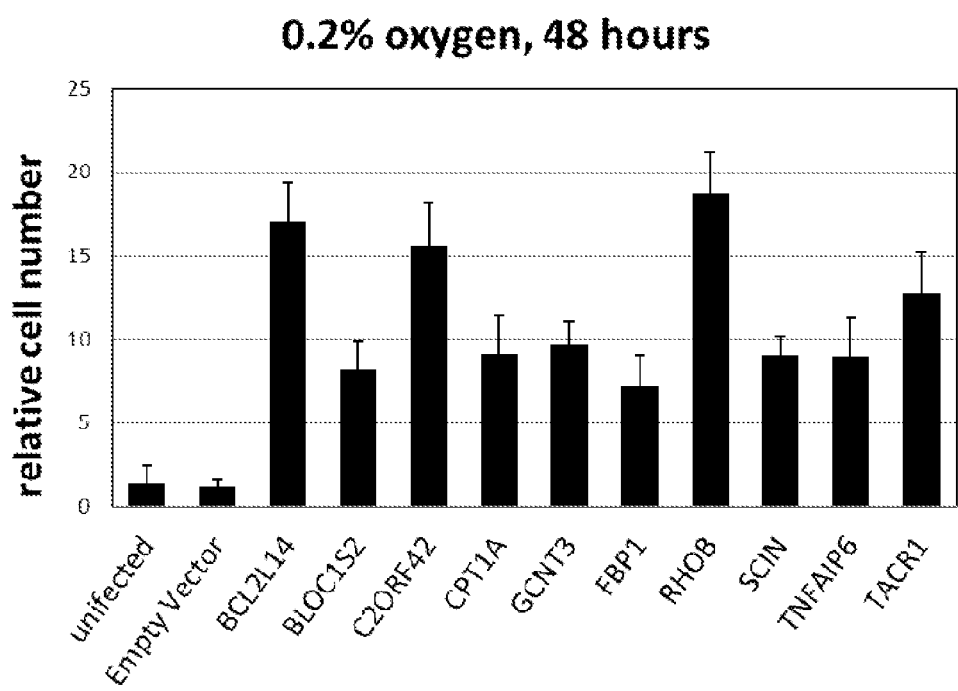
FIG. 10 provides a graphical summary of data which demonstrates efficacy of shRNAs against the designated genes to protect HKC8 cells from the effects of hypoxia.

Hypoxia generation: Day 0: HKC8 cells containing individual shRNAs were seeded in complete keratinocyte medium at a density of $2 \times 10^4$ cells per well in triplicate on two 96-well plates. Negative controls included uninfected cells or cells infected with the empty vector. Day 1: The keratinocyte medium was removed from the plates and fresh DMEM containing low glucose was added. One of the plates was then transferred to an incubator containing 0.2% oxygen for 48 hours, while the other remained at normoxia for the same period of time. All other conditions were the same. Day 3: After 48 hours, the cells were rescued from hypoxia and the plates were immediately fixed and stained with methylene blue to assess cell number. Results were then graphed as a fold change in the percent of stain of the corresponding cells incubated in normoxic conditions over that of control uninfected cells, minus the background (non-specific dye absorption by empty wells). The data presented in FIG. 10 show that the shRNAs against the indicated genes protect HKC8 cells from the effects of hypoxia.

We also tested the protective activity of a chemical TACR1 inhibitor in HKC8 cells using the following protocol. Day 0: HKC8 cells were seeded in complete keratinocyte medium at a density of $2\times10^4$ cells per well on two 96-well plates. Day 1: Keratinocyte medium was removed from the plates and fresh DMEM containing low glucose and 5 µM TACR1 inhibitor (L-733,060) was added where indicated. Treated and untreated cells were present on the plates in triplicate. The two plates were incubated in the presence of the inhibitor at normal growth conditions for 1 hour, at which time one of the plates was transported to a chamber that contained 0.2% oxygen for 48 hours, while the other remained at normoxia for the same duration. Day 3: Following exposure to hypoxia, the cells were rescued and the plates were immediately fixed and stained with methylene blue to assess survival. Results were then graphed as the percent of stain of the corresponding cells incubated in normoxic conditions minus the background (non-specific dye absorption by empty wells). The data presented in FIG. 11 demonstrate that treatment with TACR1 inhibitor is strongly protective against the effects of hypoxia on HKC8 cells While the invention has been described through specific embodiments, routine modifications will be apparent to those skilled in the art and such modifications are intended to be within the scope of the present invention.

We claim:

1. A method comprising delivering to an ex vivo organ in need of protection from hypoxia at least one agent that suppresses the expression and/or function of RHOB and also administering to the ex vivo organ an agent that suppresses the expression and/or function of TACR1.

2. The method of claim 1, wherein the at least one agent is a polynucleotide.

3. The method of claim 2, wherein the at least one agent is an shRNA.

4. The method of claim 1, wherein the organ is a kidney.

5. The method of claim 1, wherein the agent that suppresses the function of TACR1 is a member of the class of compounds that comprises compound L-733,060.

6. The method of claim 5, wherein the member of the class of compounds that comprises compound L-733,060 is L-733,060.

* * * * *

UNITED STATES PATENT AND TRADEMARK OFFICE
CERTIFICATE OF CORRECTION

| | | |
|---|---|---|
| PATENT NO. | : 9,540,640 B2 | Page 1 of 1 |
| APPLICATION NO. | : 14/423739 | |
| DATED | : January 10, 2017 | |
| INVENTOR(S) | : Kandel et al. | |

It is certified that error appears in the above-identified patent and that said Letters Patent is hereby corrected as shown below:

On the Title Page

Item (54) and in the Specification, Column 1 should read:

--COMPOSITIONS AND METHODS FOR
INHIBITING HYPOXIA INDUCED DAMAGE--

Signed and Sealed this
Twenty-first Day of March, 2017

Michelle K. Lee
*Director of the United States Patent and Trademark Office*